US006630125B2

(12) United States Patent
DeGrado et al.

(10) Patent No.: US 6,630,125 B2
(45) Date of Patent: Oct. 7, 2003

(54) 18F-LABELED CHOLINE ANALOGS

(75) Inventors: Timothy R. DeGrado, Durham, NC (US); R. Edward Coleman, Durham, NC (US); Steven W. Baldwin, Durham, NC (US); David T. Price, Greenwood, NC (US); Matthew D. Orr, Durham, NC (US); Shuyan Wang, Durham, NC (US)

(73) Assignee: Duke University, Durham, NC (US)

( * ) Notice: Subject to any disclaimer, the term of this patent is extended or adjusted under 35 U.S.C. 154(b) by 0 days.

(21) Appl. No.: 09/844,674

(22) Filed: Apr. 30, 2001

(65) Prior Publication Data

US 2002/0061279 A1 May 23, 2002

Related U.S. Application Data

(60) Provisional application No. 60/231,303, filed on Sep. 8, 2000, and provisional application No. 60/200,347, filed on Apr. 28, 2000.

(51) Int. Cl.$^7$ ............................................... A61K 51/00
(52) U.S. Cl. ....................................................... 424/1.89
(58) Field of Search ............................... 424/1.89, 1.81, 424/1.85

(56) References Cited

U.S. PATENT DOCUMENTS

| 4,446,123 A | * | 5/1984 | Woo ........................... 424/1.11 |
| 5,750,089 A | | 5/1998 | Neumeyer et al. | |

FOREIGN PATENT DOCUMENTS

| JP | 9-48747 | 2/1997 |
| JP | 2809145 | 7/1998 |

OTHER PUBLICATIONS

Hara et al, "Automated Synthesis of [$^{11}$C]choline, a positron–emitting tracer for tumor imaging", Applied Radiation and Isotopes 50(3):531–533 (1999).

Hara et al, "Automated Synthesis of Fluorine–18 Labeled Choline Analogue 2–Fluoroethyl–Dimethyl–2–Oxyethylammonium", Scientific Papers, Proceedings of the 44$^{th}$ Annual Meeting, The Journal of Nuclear Medicine No. 156, p. 44P, Tuesday, Jun. 3, 1997.

Friedland et al, "Labeled Choline and Phosphorylcholine: Body Distribution and Brain Autoradiography: Concise Communication", J. Nucl. Med. 24:812–815 (1983).

Roivainen et al, "Blood metabolism of [*methyl*–$^{11}$C]choline; implications for in vivo imaging with positron emission tomography", Eur. J. Nucl. Med. 27(1):25–32 (2000).

Hara et al, "Sensitive Detection of Mediastinal Lymph Node Metastasis of Lung Cancer with $^{11}$C–Choline PET", J. Nucl. Med. 41(9):1507–1513 (2000).

Shinoura et al, "Brain Tumors: Detection with C–11 Choline PET", Radiology 202(2):497–503 (1997).

Rosen et al, "Carbon–11 Choline: Synthesis, Purification, and Brain Uptake Inhibition by 2–Dimethylaminoethanol", J. Nucl. Med. 26(12):1424–1428 (1985).

Hara et al, "PET Imaging of Prostate Cancer Using Carbon–11–Choline", J. Nucl. Med. 39(6):990–995 (1998).

Kobori et al, "Positron Emission Tomography of Esophageal Carcinoma Using $^{11}$C–Choline and 18$^f$–Fluorodeoxyglucose", Cancer 86:1638–1648 (1999).

Hara et al, "PET Imaging of Brain Tumor with [*methyl*–$^{11}$C] Choline", J. Nucl. Med. 38(6):842–847 (1997).

Translation of Hara et al, "Fluorine–18–Labeled Fluorine––Containing Choline Derivatives, Methods For Their Preparation, And Their Use As Diagnostic Agents For Positron Emission Computed Tomography", Japanese Patent Office, Patent Journal (A), Kokai Patent Application No. HEI 9[1997]–48747.

* cited by examiner

*Primary Examiner*—Michael G. Hartley
(74) *Attorney, Agent, or Firm*—Nixon & Vanderhye

(57) ABSTRACT

The present invention relates to $^{18}$F-labeled choline analogs and to methods of using same as imaging agents (for example, as positron emission tomography (PET) imaging agents) for the noninvasive detection and localization of neoplasms and pathophysiologies influencing choline processing in the body. The invention further relates to methods of synthesizing $^{18}$F-labeled choline analogs and to compositions comprising such analogs.

30 Claims, 12 Drawing Sheets

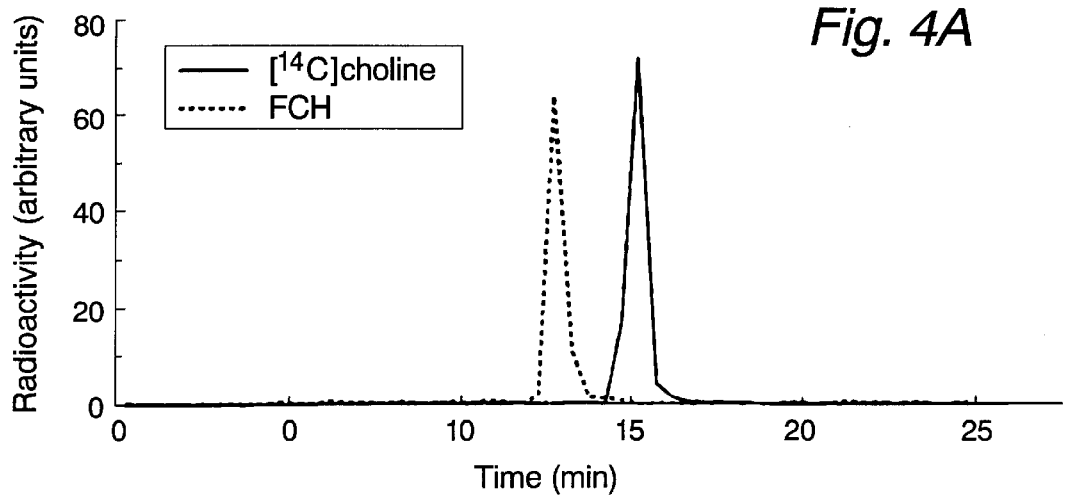
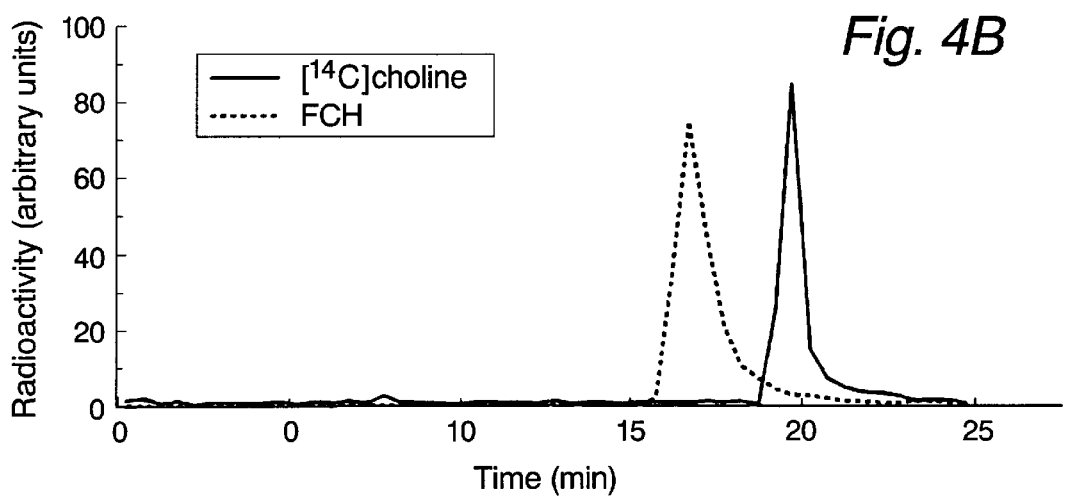
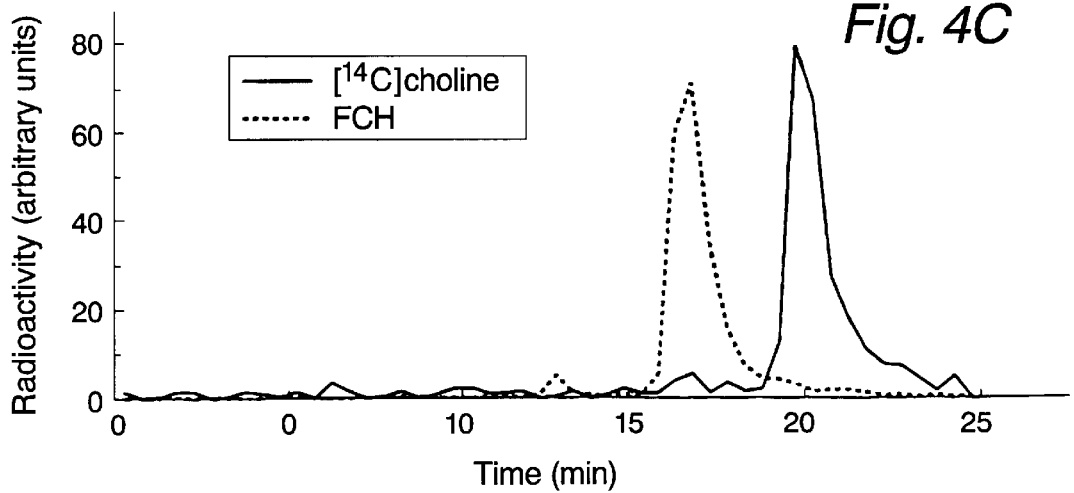

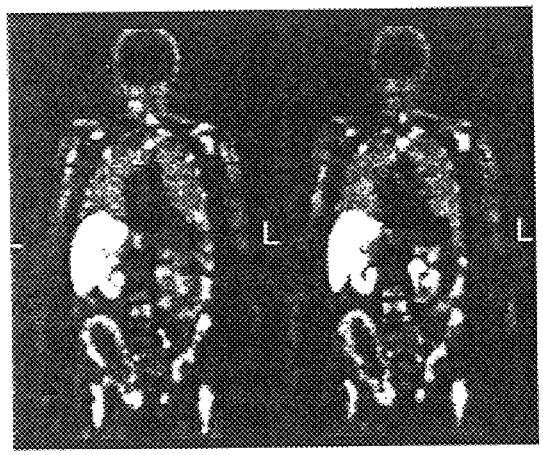 
Fig. 8A                    Fig. 8B

*Fig. 11*
PET Images in Patient with Hormone Refractory Prostate Cancer - FDC5
FDC - PET     SUV of right pubic ramus metastasis = 11.7
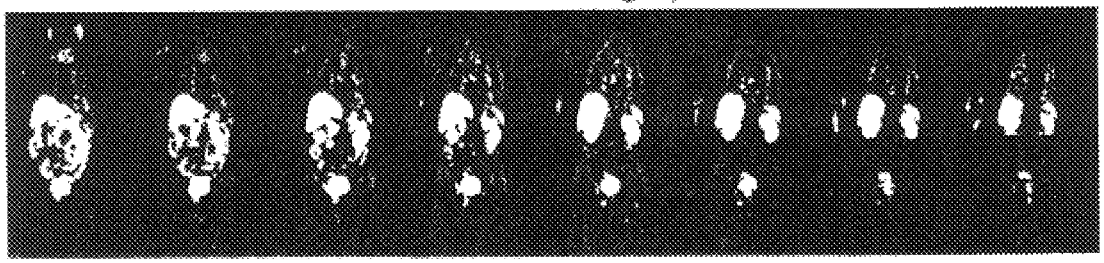
FDG - PET     SUV of right pubic ramus metastasis = 6.5
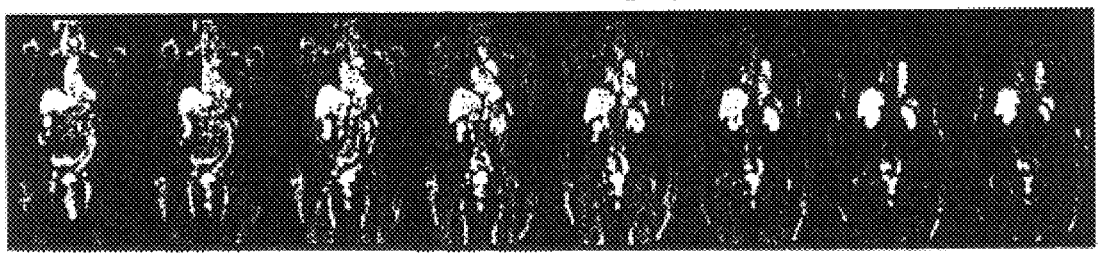
Duke University Medical Center
*Fig. 12*
MRI
[$^{18}$F]FCH
[$^{18}$F]FDG
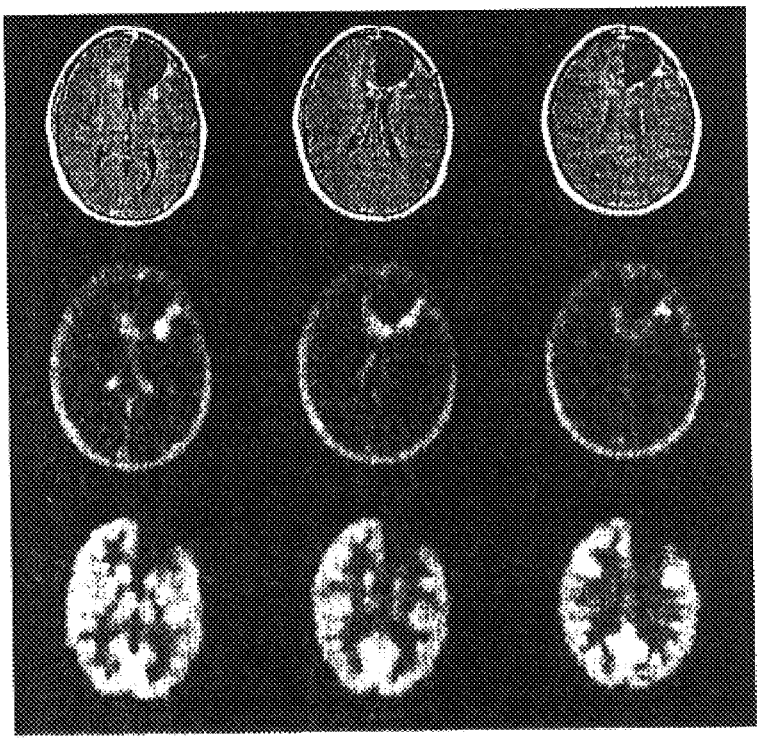

[18]F-LABELED CHOLINE ANALOGS

This application claims priority from U.S. Provisional Application No. 60/200,347 filed Apr. 28, 2000, and from U.S. Provisional Application No. 60/231,303, filed Sep. 8, 2000. The contents of both applications are incorporated herein by reference.

TECHNICAL FIELD

The present invention relates to $^{18}$F-labeled choline analogs and to methods of using same as imaging agents (for example, as positron emission tomography (PET) imaging agents) for the noninvasive detection and localization of neoplasms and pathophysiologies influencing choline processing in the body. The invention further relates to methods of synthesizing $^{18}$F-labeled choline analogs and to compositions comprising such analogs.

BACKGROUND

Positron emission tomography (PET) is uniquely suited to evaluate metabolic activity in human neoplasms for diagnostic imaging purposes. The glucose analog, [$^{18}$F]fluoro-2-deoxy-glucose (FDG), has proven successful as a PET imaging agent for detection and localization of many forms of cancer. The elevated rate of glycolysis in many types of tumor cells enhances the uptake of FDG in neoplasms relative to normal tissues (Weber et al, Strahlenther Onkol. 175:356–373 (1999), Delbeke, J. Nucl. Med. 40:591–603 (1999), Hoh et al, J. Urology 159:347–356 (1998)). However, FDG-PET has been found to have less sensitivity and/or specificity for assessment of some types of cancer, motivating efforts to develop new oncologic tracers for PET. Carbon-11 (T½=20 min) labeled choline (CH, trimethyl-2-hydroxyethylammonium) has shown potential utility in two applications: brain tumors (Hara et al, J. Nucl. Med. 38(6):842–847 (1997), Shinoura et al, Radiology 202(2):497–503 (1997)), where FDG has suboptimal specificity due to uptake by normal brain and some post-therapy responses (Marriott et al, J. Nucl. Med. 39(8):1376–1390)1998)), and prostate carcinoma (Hara et al, J. Nucl. Med. 39(6):990–995 (1998)), where FDG shows inadequate sensitivity (Hoh et al, J. Urology 159:347–356 (1998), Shreve et al, Radiology 199:751–756 (1996)). CH was initially synthesized and evaluated as a physiologic probe for choline uptake by normal tissues (Friedland et al, J. Nucl. Med. 24(9):812–815 (1983), Rosen et al, J. Nucl. Med. 26(12):1424–1428 (1985)). The practical advantages of working with the longer lived radioisotope fluorine-18 (T½=110 min) led Hara et al (J. Nucl. Med. 38:44P (1997)) to synthesize and preliminarily evaluate the choline analog, 2-[$^{18}$F]fluoroethyl-dimethyl-2-hydroxyethyl-ammonium (designated herein HARA-1). This analog showed similar biodistribution of this tracer to CH in normal human subjects with the exception of more prominent urinary excretion of radioactivity. The more rapid accumulation of radioactivity in the urinary bladder with this $^{18}$F-labeled analog rendered it less preferable than CH for imaging of primary prostate carcinoma and metastatic prostate carcinoma in the pelvic lymph nodes (Hara et al, J. Nucl. Med. 38:44P (1997)).

The present invention provides $^{18}$F-labeled analogs of choline for imaging, including oncologic imaging with PET.

SUMMARY OF THE INVENTION

The present invention relates to $^{18}$F-labeled choline analogs and to methods of using same, for example, as PET imaging agents for the noninvasive detection and localization of neoplasms and pathophysiologies influencing choline processing in the body. The invention further relates to methods of synthesizing $^{18}$F-labeled choline analogs and to compositions comprising such analogs.

Objects and advantages of the present invention will be clear from the description that follows.

BRIEF DESCRIPTION OF THE DRAWINGS

FIGS. 4A–4C. Normal phase, gradient HPLC analysis (Promfret et al, Anal. Biochem. 180:85–90 (1989)) of (FIG. 4A) FCH and [$^{14}$C]CH; (FIG. 4B) phosphoryl-FCH and [$^{14}$C]phosphoryl-CH enzymatically synthesized using yeast choline kinase according to the method of Ishidate (Methods Enzymol. 209:121–123 (1992)); (FIG. 4C) hydrophilic radiolabeled metabolites in cultured PC-3 prostate cancer cells following incubation with FCH and [$^{14}$C]CH. The close correspondence of chromatograms of FIGS. 4B and 4C indicate extensive intracellular phosphorylation of both FCH and [$^{14}$C]CH in the cancer cells.

FIG. 7. Attenuation-corrected [$^{18}$F] FCH-PET image (coronal projections, 3–5 min post-injection) of pelvis region of patient #1 having an untreated primary prostate carcinoma (P) and an osseous metastasis in the left ischium (M). Slice thickness is 12.9 mm. In these early images, radioactivity had not yet arrived at the urinary bladder, allowing excellent delineation of the prostate gland. The metastasis was also apparent on bone scan, CT and MRI. FIG. 7B. Time-activity curves for FCH in the same patient, showing the arrival of radioactivity in the urine to be at about 8 min p.i.

FIGS. 8A and 8B. Comparison of FCH (FIG. 8A) and FDG (FIG. 8B) PET images in patient #3 having advanced metastatic prostate carcinoma. Images are not attenuation-corrected. The images are coronal projections having slice thickness of 12.9 mm. The patient had undergone radical retropubic prostatectomy and limited pelvic lymphadenectomy 12 years prior. The plasma PSA level was 4172. Bone scans showed extensive osseous metastases. Both scans reveal soft-tissue and osseous metastases, but FCH allowed detection of more lesions, and showed 2-fold higher tracer uptake in osseous lesions as estimated by the SUV index (FCH=8.0, FDG=4.1).

(FIG. 10A) Attenuation-corrected [$^{18}$F] FCH-PET image (coronal projection, 2–4 min post-injection) of pelvis region of patient #1 having biopsy-proven recurrent local prostate carcinoma. Slice thickness is 12.9 mm. In this early image, radioactivity had not yet arrived at the urinary bladder, allowing excellent delineation of recurrent disease in the prostate bed (arrow). (FIG. 10B) Time-activity curves for FCH in the same patient, demonstrating very rapid clearance of radioactivity from a region-of-interest placed on the iliac artery, rapid accumulation of tracer in the local prostate bed, and arrival of radioactivity in the urinary bladder after 4 min post-injection. (FIG. 10C) Attenuation-corrected whole-body scan (coronal projections) showing several foci of high FCH uptake in the mediastinum suggestive of prostate cancer in hilar and para-aortic lymph nodes.

FIG. 11. FDC-PET imaging of patient with advanced metastatic prostate cancer.

FIG. 12. A patient with biopsy-confirmed recurrent anaplastic astrocytoma was imaged by T1-weighted Gd-DTPA enhanced MRI, [$^{18}$F]FCH-PET (5–10 min post-injection) and [$^{18}$F]FDG-PET (30–36 min post-injection). The MRI showed nodular enhancement posteriorly at the postoperative cyst wall. The FCH scan demonstrated diffuse abnormal accumulation posteriorly and medially to the cyst with focal areas of accumulation corresponding to the nodular areas of enhancement on the MRI. Note the absence of normal cortex accumulation that is seen with FDG. The FDG scan shows a thin rim of abnormal accumulation that would support recurrent tumor, but the abnormality is difficult to detect when compared to the FCH and MRI scans.

DETAILED DESCRIPTION OF THE INVENTION

Figure 1:
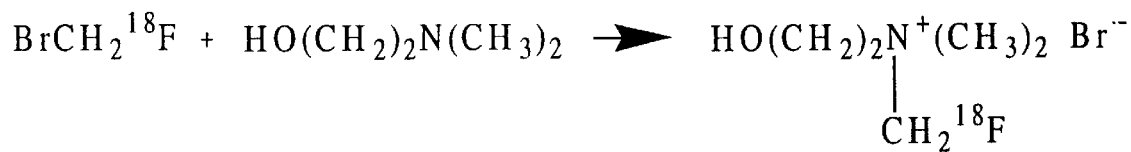
FIG. 1. Reaction sequence for synthesis of dimethylfluoromethyl-2-hydroxyethylammonium chloride (FCH).

PET can be used to detect and stage cancer because of its unique strength in providing noninvasive assessment of metabolic and physiologic rates through tracer techniques. PET can also be used to monitor a patient's response to therapy. Differentiation of malignant cancer tissue from neighboring nonmalignant tissues can be accomplished by exploiting changes in biochemical fluxes that occur in response to metabolic, genetic, or microstructural changes in the malignant cells.

Choline is taken up by a high affinity choline transporter into tissues and utilized for synthesis of phospholipids and sphingomyelin. Intracellular choline is rapidly metabolized to phosphocholine (PC) or oxidized by choline oxidase to betaine (mainly in liver and kidneys). Phosphorylation of choline, catalyzed by choline kinase (CK), is an obligatory step for incorporation of choline into phosphatidylcholine. Once phosphorylated, the polar PC molecule is trapped within the cell. Studies using magnetic resonance spectroscopy (MRS) (Negendank, NMR Biomed. 5:303–324 (1992)) and biochemical analyses (Kano-Sueoka et al, Jpn J. Cancer Res. 82:829–834 (1991), Macara, Mol. Cell Biol. 9:325–328 (1989), Ratnam et al, Arch. Biochem. Biophys. 323:313–322 (1995), Nakagami et al, Jpn J. Cancer Res. 90:419–424 (1999)) have revealed elevated levels of choline, PC, and phosphoethanolamine in many types of cancer cells. The activity of CK has been found to be upregulated in malignant cells (Macara, Mol. Cell Biol. 9:325–328 (1989), Ratnam et al, Arch. Biochem. Biophys. 323:313–322 (1995), Nakagami et al, Jpn J. Cancer Res. 90:419–424 (1999)), providing a potential mechanism for the enhanced accumulation of radiolabeled choline analogs by neoplasms.

In one embodiment of the present invention, $^{18}$F-labeled choline analogs are used as PET imaging agents. The PET imaging technique utilizes scanning devices that detect the 511 keV annihilation photons that are emitted after radioactive decay of fluorine-18. PET scanners are widely available for imaging of human subjects. In addition, "microPET" scanners that have high spatial resolution can be used for imaging of small animals. In addition to PET scanners, $^{18}$F-radioactivity can also be monitored using one or more radiation detector probes.

Suitable choline analogs include those of Formula I and II (and pharmaceutically acceptable salts thereof):

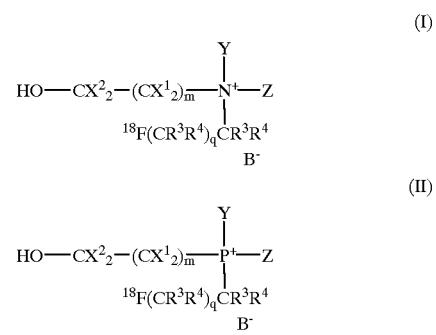

wherein

B$^-$ is a conjugate base of an acid (i.e., counteranion)

Y=H, CH$_2$R$^1$ or CX$^3{}_2$CX$^4{}_2$—OH

Z=H, CH$_2$R$^2$, CH(CH$_3$)$_2$, CH$_2$CH=CH$_2$, CX$^5{}_2$CX$^6{}_2$OH, OCH$_3$, SCH$_3$, CH$_2$C≡CH, CH$_2$C(CH$_3$)=CH$_2$, CH$_2$(C$_6$H$_5$), CH$_2$CH(CH$_3$)$_2$, CH$_2$OCH$_3$ or CH$_2$SCH$_3$

X$^1$, X$^2$, X$^3$, X$^4$, X$^5$ and X$^6$=independently, H or deuterium

R$^1$=H, F, Cl, Br, I or CH$_3$

R$^2$=H, F, Cl, Br, I, CH$_3$ or CH$_2$CH$_3$

R$^3$=independently, H or $^{19}$F

R$^4$=independently, H or $^{19}$F m=1 or 2 q=0–2 or

Z and Y together=(CH$_2$)n, wherein n=2–6, or (CH$_2$)$_a$O(CH$_2$)$_b$, wherein a=0–4 and b=0–4, or (CH$_2$)$_a$S(CH$_2$)$_b$, wherein a=0–4 and b=0–4.

The preferred analogs are of Formula I wherein Y is $CH_2R^1$ or $CX^3_2CX^4_2$—OH wherein $R^1$ is H, F, Cl, Br, I or $CH_3$, Z is $CH_3$, $CH_2F$, $CH_2Cl$, $CH_2Br$, $CH_2I$, $CH_2CH_3$, $CH_2CX^6_2$—OH, $CH_2CH$=$CH_2$, $CH_2C(CH_3)$=$CH_2$, $CH_2C$≡$CH$, $CH_2CH(CH_3)_2$ or $(CH_2)_2CH_3$, or YZ is $(CH_2)_n$ wherein n=2–6, $X^1$, $X^2$, $X^3$, $X^4$ and $X^6$ are, independently, H or deuterium, $R^3$ and $R^4$ are H, m is 1 or 2 and q=0 or 2 (and wherein B⁻ is a pharmaceutically acceptable counteranion (such as Cl⁻ or Br⁻)).

The more preferred analogs are of Formula I wherein Y is $CH_3$ or $CH_2CX^4_2$—OH, Z is $CH_3$, $CH_2CH_3$, $CH_2CX^6_2$—OH, $CH_2CH$=$CH_2$, $CH_2C(CH_3)$=$CH_2$, $CH_2C$≡$CH$, $CH_2CH(CH_3)_2$ or $(CH_2)_2CH_3$, $X^1$, $X^2$, $X^4$ and $X^6$ are, independently, H or deuterium, $R^3$ and $R^4$ are H, m is 1 or 2 and q=0 or 2 (and wherein B⁻ is a pharmaceutically acceptable conjugate base). Most preferably, Y is $CH_3$ and Z is $CH_3$, $X^1$ is H and $X^2$ is H or deuterium, $R^3$ and $R^4$ are H, m is 1 and q is 0 (and wherein B⁻ is Cl⁻).

The $^{18}F$-labeled analogs of the invention can be synthesized using, for example, gas chromatographically isolated [$^{18}F$]fluoroalkylating agents (e.g., [$^{18}F$]fluorobromomethane). Reaction of [$^{18}F$]fluoroalkylating agents with appropriate tertiary amines affords readily isolatable $^{18}F$-labeled choline analogs as quartenary ammonium salts. The reaction of an [$^{18}F$]fluoroalkylating agent with tertiary amines can be performed in a solvent that readily dissolves the [$^{18}F$]fluoroalkylating agent, allows efficient alkylation, and is readily removed following the reaction under a stream of inert gas. Examples of suitable solvents include acetone and acetonitrile. The isolation of the final ammonium ion product from the precursor tertiary amine can be achieved using, for example, a cation exchange SEP-PAK. The SEP-PAK can be washed with a suitable alcohol (e.g., ethanol) and water to completely remove uncharged molecules, including the tertiary amine. The final product can be eluted from the SEP-PAK using a sterile isotonic saline (NaCl) solution, however, other suitable pharmaceutic solutions can also be used.

More specifically, the invention includes a method of synthesizing a compound of Formula I or II $$HO-CX^2_2-(CX^1_2)_{\overline{m}}-\overset{\overset{Y}{|}}{\underset{\underset{B^-}{|}}{N^+}}-Z \qquad (I)$$
$$\phantom{HO-CX^2_2-(CX^1_2)_{\overline{m}}-}{}^{18}F(CR^3R^4)_qCR^3R^4$$

$$HO-CX^2_2-(CX^1_2)_{\overline{m}}-\overset{\overset{Y}{|}}{\underset{\underset{B^-}{|}}{P^+}}-Z \qquad (II)$$
$$\phantom{HO-CX^2_2-(CX^1_2)_{\overline{m}}-}{}^{18}F(CR^3R^4)_qCR^3R^4$$

wherein
B⁻ is a counteranion
Y=$CH_2R^1$ or $CX^3_2CX^4_2$—OH
Z=$CH_2R^2$, $CH(CH_3)_2$, $CH_2CH$=$CH_2$, $CX^5_2CX^6_2OH$, $OCH_3$, $SCH_3$, $CH_2C$≡$CH$, $CH_2C(CH_3)$=$CH_2$, $CH_2(C_6H_5)$, $CH_2CH(CH_3)_2$, $CH_2OCH_3$ or $CH_2SCH_3$
$X^1$, $X^2$, $X^3$, $X^4$, $X^5$ and $X^6$=independently, H or deuterium
$R^1$=H, F, Cl, Br, I or $CH_3$
$R^2$=H, F, Cl, Br, I, $CH_3$ or $CH_2CH_3$
$R^3$=independently, H or $^{19}F$
$R^4$=independently, H or $^{19}F$ m=1 or 2
q=0–2 comprising:

i) synthesizing a [$^{18}F$]fluoroalkylating agent of Formula III:

$$^{18}F(CR^3R^4)_qCR^3R^4-LG \qquad (III)$$

wherein
$R^3$=independently, H or $^{19}F$
$R^4$=independently, H or $^{19}F$
LG=leaving group (e.g., Br, I, tosyloxy, mesyloxy or other sulfonate ester)

by nucleophilic radiofluorination of a precursor of Formula IV:

$$LG-(CR^3R^4)_qCR^3R^4-LG \qquad (IV)$$

wherein
$R^3$=independently, H or $^{19}F$
$R^4$=independently, H or $^{19}F$
LG=leaving group (e.g., Br, I, tosyloxy, mesyloxy, or other sulfonate ester)

using [$^{18}F$]fluoride or H$^{18}$F and a catalyst, such as Kryptofix 2.2.2 or a basic tetraalkylammonium salt (e.g., tetrabutylammonium bicarbonate), ii) isolating the [$^{18}F$]fluoroalkylating agent from the precursor and the catalyst (and any remaining salts and solvents introduced in step (i)) (e.g., using gas or liquid chromatography), iii) reacting the isolated [$^{18}F$]fluoroalkylating agent from step (ii) with the appropriate precursor tertiary amine (Formula I (e.g., $$HO-CX^2_2-(CX^1_2)_{\overline{m}}-\overset{\overset{Y}{|}}{N}-Z))$$

or tertiary phosphine (Formula II (e.g., $$HO-CX^2_2-(CX^1_2)_{\overline{m}}-\overset{\overset{Y}{|}}{P}-Z))$$

alkylation substrate in a suitable solvent (e.g., acetonitrile or acetone) to form the compound of Formula I or II, and iv) isolating said compound of Formula I or II from the precursor tertiary amine (Formula I) or tertiary phosphine (Formula II), for example, by evaporating the solvent and transferring the compound of Formula I or II in a suitable alcohol (e.g., ethanol) to a cation exchange resin cartridge and washing the cartridge with a suitable alcohol (e.g., ethanol) and subsequently with sterile water, and eluting the compound of Formula I or II from the cartridge with a pharmaceutically suitable carrier (e.g., sterile isotonic NaCl solution).

The invention also includes a method of synthesizing a compound of Formula I or II

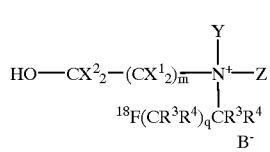
(I)

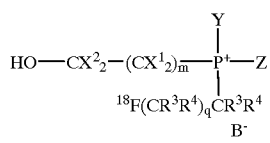
(II)

wherein
    $B^-$ is a counteranion
    $Y=CH_2R^1$ or $CX^3{}_2CX^4{}_2$—OH
    $Z=CH_2R^2$, $CH(CH_3)_2$, $CH_2CH=CH_2$, $CX^5{}_2CX^6{}_2OH$, $OCH_3$, $SCH_3$, $CH_2C\equiv CH$, $CH_2C(CH_3)=CH_2$, $CH_2(C_6H_5)$, $CH_2CH(CH_3)_2$, $CH_2OCH_3$ or $CH_2SCH_3$
    $X^1, X^2, X^3, X^4, X^5$ and $X^6$=independently, H or deuterium
    $R^1$=H, F, Cl, Br, I or $CH_3$
    $R^2$=H, F, Cl, Br, I, $CH_3$ or $CH_2CH_3$
    $R^3$=independently, H or $^{19}F$
    $R^4$=independently, H or $^{19}F$
    m=1 or 2
    q=1 or 2
comprising:
    i) preparing a hydroxyl-protected $^{18}F$-labeled choline analog of the formula VI or VII:

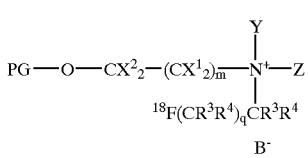
(VI)

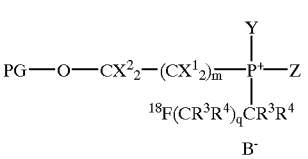
(VII)

wherein
    $B^-$ is a counteranion (e.g., bicarbonate)
    $Y=CH_2R^1$ or $CX^3{}_2CX^4{}_2$—OH
    $Z=CH_2R^2$, $CH(CH_3)_2$, $CH_2CH=CH_2$, $CX^5{}_2CX^6{}_2OH$, $OCH_3$, $SCH_3$, $CH_2C\equiv CH$, $CH_2C(CH_3)=CH_2$, $CH_2(C_6H_5)$, $CH_2CH(CH_3)_2$, $CH_2OCH_3$ or $CH_2SCH_3$
    $X^1, X^2, X^3, X^4, X^5$ and $X^6$=independently, H or deuterium
    $R^1$=H, F, Cl, Br, I or $CH_3$
    $R^2$=H, F, Cl, Br, I, $CH_3$ or $CH_2CH_3$
    $R^3$=independently, H or $^{19}F$
    $R^4$=independently, H or $^{19}F$
    m=1 or 2
    q=1 or 2
    PG=hydroxyl protecting group (e.g., an acetyl group)
by nucleophilic radiofluorinating of a compound of the formula VIII or IX:

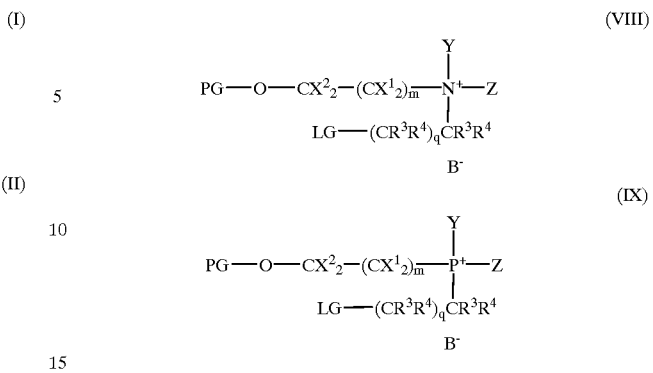

wherein
    $B^-$ is a counteranion (e.g., bicarbonate)
    $Y=CH_2R^1$ or $CX^3{}_2CX^4{}_2$—OH
    $Z=CH_2R^2$, $CH(CH_3)_2$, $CH_2CH=CH_2$, $CX^5{}_2CX^6{}_2OH$, $OCH_3$, $SCH_3$, $CH_2C\equiv CH$, $CH_2C(CH_3)=CH_2$, $CH_2(C_6H_5)$, $CH_2CH(CH_3)_2$, $CH_2OCH_3$ or $CH_2SCH_3$
    $X^1, X^2, X^3, X^4, X^5$ and $X^6$=independently, H or deuterium
    $R^1$=H, F, Cl, Br, I or $CH_3$
    $R^2$=H, F, Cl, Br, I, $CH_3$ or $CH_2CH_3$
    $R^3$=independently, H or $^{19}F$
    $R^4$=independently, H or $^{19}F$
    m=1 or 2
    q=1 or 2
    PG=hydroxyl protecting group (e.g., acetyl)
    LG=leaving group (e.g., bromo-, iodo-, tosyloxy-, mesyloxy-, other sulfonate ester)
    using [$^{18}F$]fluoride or $H^{18}F$ in the presence of a catalyst (e.g., Kryptofix 2.2.2/$K_2CO_3$ or a basic tetraalkylammonium salt (e.g., tetrabutylammonium bicarbonate),
    ii) deprotecting the alcohol functional group to form the compound of Formula I or Formula II (the deprotection, for example, can be effected through acid or base catalyzed hydrolysis),
    iii) isolating the product resulting from step (ii) from the labeling precursor, catalyst (and remaining salts and solvents introduced in steps (i) and (ii)), and
    iv) formulating the product of step (iii) in a pharmaceutically acceptable carrier for example, involving the use of anion and/or cation exchange resin cartridges to isolate the product from nonphysiologic solvents or salts remaining with the product after step (iii) (HPLC can be used). In one embodiment, the hydroxyl-protected, leaving group-substituted precursor is 3-bromopropyl-dimethyl-2-acetoxyethyl-ammonium bicarbonate.

The analogs of the invention can be present in a composition together with a pharmaceutically acceptable carrier. Advantageously, the carrier is sterile and the composition is suitable for IV injection. An example of suitable carrier is a sterile solution of 0.9% NaCl in water. Analogs of the invention can also be formulated with a chemical stabilizer in order to reduce the likelihood for radiolysis-induced decomposition of the $^{18}F$-labeled choline analog product at high radioactivity concentrations. Suitable stabilizers include antioxidants such as the pharmaceutically acceptable antioxidant, sodium L-ascorbate.

In the context of PET imaging, analogs of the invention are preferably administered as an intravenous (IV) bolus. Typically, the patient is fasted at least 4 hours prior to administration of the analog.

The present analogs can be used in the detection and localization of a wide variety of neoplasms where elevated choline uptake and choline phosphorylation occur, including but not restricted to prostate cancer, brain tumors, metastatic renal cell carcinomas and breast, lung and colorectal tumors, melanomas and lymphomas. The analogs are particularly useful for imaging pelvic tumors (the pelvis can be defined as that region that extends from the bottom of the ishia to the top of the iliac crest), including prostate tumors and metastases thereof in the pelvic lymph nodes, ovarian cancer, cervical cancer and bladder cancer.

In imaging the pelvis region using PET or another external radiation detection technique, emission images of the pelvis region can be acquired after injection of the present analog but before the arrival of excreted radioactive material in the ureters and urinary bladder. This method allows images to be obtained of the distribution of the compound in the pelvic region without confounding radioactivity in the ureters or urinary bladder. The method does not require additional interventions for clearing the radioactive material from the bladder, such as urethral catheterization and irrigation of the bladder, in order to obtain diagnostically acceptable imaging information.

The present analogs can also be used to guide the biopsy of malignancies and monitor the effects of various therapeutic regimens, including chemotherapy. In accordance with the present invention, neoplasms can be detected and localized in the context of oncologic surgical procedures using an intraoperative radioactivity detection probes. The patient can be administered the $^{18}$F-labeled analog and an appropriately shielded radiation detector can be subsequently used during the surgical procedure to detect and/or localize neoplasm(s) in the body, such as to identify lymph nodes that bear malignant tissue. When the method is performed in the pelvic region, the technique may require urethral catheterization and irrigation of the urinary bladder in order to remove the confounding radioactivity in urine from the body.

The present analogs can also be used in the noninvasive assessment of the response of neoplastic tissue in a patient to therapeutic interventions using PET scanning or another external radiation detection technique. The patient can be scanned at more than one time and the data from two or more scans are compared to determine potential differences in the tumor uptake of the analog. Comparisons can involve either qualitative image comparison (e.g. contrast of tumor uptake from background) or quantitative indices derived from the imaging or external radiation detection data (e.g. standardized uptake values (SUVs)).

The present analogs can also be used in the staging of neoplasms based on quantitative or qualitative measurements of uptake of the present analogs by tissue. The tissue uptake of the analog can be determined while the tissue is within the body or outside the body. The uptake measurements can be performed in conjunction with pathologic/histologic/histochemical/immunohistochemical assessment of the same tissue for classification and evaluation of malignancy. The method of the present invention can be used to determine the degree of malignancy of a tissue by quantitating the amount of $^{18}$F radioactivity present.

The present analogs can also be used in the anatomical mapping of the distribution of neoplastic tissue in the body using PET or another external radiation detection technique in combination with anatomical images obtained using CT, MRI, or ultrasound. The anatomical images can be acquired using a dedicated CT/PET, MRI/PET, PET/ultrasound scanning device or separate PET and CT/MRI/ultrasound scanning devices. If separate PET and CT/MRI/ultrasound imaging devices are used, image analysis techniques can be employed to spatially register the PET images with the anatomical images. The method can be used for intraorgan mapping of neoplastic tissue, for example, the spatial distribution of prostate carcinoma within the prostate gland can be determined for aiding in biopsy of the prostate gland or planning of radiation therapy of the prostate gland either by external beam radiation or brachytherapy. Likewise, the method may be used for guiding the biopsy or surgical resection of lymph nodes.

In alternative embodiments of the instant invention, the above-described analogs can also be used in radiolabeling of neoplasms and in vitro counting of radioactivity. The tracer can be administered in vivo or ex vivo in tissue or cell culture experimental models.

In further embodiments of the instant invention, the above-described analogs can be used in the assessment of choline processing in liver, spleen and kidneys in pathophysiologic conditions not related to cancer. Rates of choline transport and metabolism are relatively high in these organs, indicating an importance of choline processing pathways in these tissues. Abnormalities in phospholipid metabolism can occur in liver, spleen and kidneys either directly due to diseases that directly influence lipid metabolism or pathologies that indirectly alter choline processing through morphologic, histologic, or metabolic mechanisms.

The compounds and methods of the invention have use in humans and non-human animals (including dogs).

Certain aspects of the present invention are described in greater detail in the non-limiting Examples that follow.

EXAMPLES

The following experimental details are relevant to the Examples that follow.

Equipment

Nuclear magnetic resonance spectra were recorded on a Varian INOVA 400 MHz spectrometer. High resolution fast atom bombardment (FAB) mass measurements were made using a JEOL JMS-SX102A mass spectrometer operating at 10 k resolution.

Dimethylfluoromethyl-2-hydroxyethylammonium Chloride (Fluorocholine Chloride, [$^{19}$F]FCH)

To a 50 ml pressure tube containing 20 mL dry THF at −78° C. was added 5 ml (0.0498 mol) N,N-dimethylethanolamine (Aldrich). Chlorofluoromethane (Synquest Labs, Alachua Fla.) was bubbled through the solution for 15 minutes whereupon the tube was sealed with a teflon screw cap. The mixture was allowed to warm to room temperature over 18 hours, during which time a white solid precipitated. The solid was isolated by filtration, washed several times with cold THF, and dried under vacuum. N,N-dimethyl-N-fluoromethylethanolamine was isolated as a hygroscopic, amorphous white solid. (1.386 g, 17.7%); mp 184–185° C. (dec.); $^1$H NMR (400 MHz, D$_2$0), 3.08 (d, J=2.1 Hz, 6 H), 3.45–3.48 (m, 2 H), 3.90–3.93 (m, 2 H), 5.28 (d, J=44.9 Hz, 2 H); $^{13}$C NMR (100 MHz, D$_2$0), 47.18, 55.28, 63.09, 95.77, 97.97; $^{19}$F NMR (376.5 MHz, D$_2$0) 106.45 (mt, J=45.2 Hz); HRMS (FAB) Calcd for M$^{30}$ C$_5$H$_{13}$ONF: 122.0981, Found 122.0984.

Synthesis of [$^{18}$F]FCH

FCH was synthesized via the intermediate [$^{18}$F] fluorobromomethane (FBM) (FIG. 1). The synthesis of FBM was essentially that of Eskola et al (J. Labelled Cpd Radiopharm. 42:S543–S545 (1999)), which was modified from Coenen et al (J. Labelled Cmp Radiopharm. 23:587–595 (1985)). The alkylation with FBM of dimethylethanolamine, isolation of the resultant FCH, and performance of quality control HPLC were modified from the techniques used by Hara et al (J. Nucl. Med. 38(6):842–847 (1997)) for synthesis and quality control of [$^{11}$C]CH from [$^{11}$C] methyliodide. FBM was produced by reaction of dibromoethane (0.05 ml) with no-carrier-added [$^{18}$F]fluoride assisted by (Kryptofix 2.2.2/K)$_2$CO$_3$ (10 μmol) in dry acetonitrile (0.7 ml). [$^{18}$F]fluorobromomethane was isolated by gas chromatography (Porapak Q, 80/100 mesh, 7.8×700 mm, 100° C., helium flow=75 cc/mm, retention time=6 mm) and trapped in a solution of 0.1 ml dimethylethanolamine in acetone (1.5 ml) within a 2.5 ml conical glass vial kept at −5–0° C. using a Peltier cooling/heating device (McKinney et al, Appl. Rad. Isot., 54:97–100 (2001)). The vial was sealed and heated to 100° C. for 10 mm. The solvent was evaporated under a stream of helium, and the residue taken up in ethanol (2×2 ml) and transferred to a cation exchange SEP-PAK cartridge (Walters, Accell Plus CM Light). After further washing of the cartridge with ethanol (10 ml) and sterile water (10 ml), the product was eluted with sterile isotonic saline (>2 ml) and passed through a 0.22 μm sterile filter (Millipore, Millex GS).

[methyl-$^{14}$C]Choline (CH) was obtained from NEN Research (Boston, Mass.). In an analogous fashion to the synthesis of FCH, [$^{18}$F]fluoroethyl-dimethyl-2-hydroxyethyl-ammonium ([$^{18}$F]FEC, HARA-1) was synthesized via the intermediate 1-[$^{18}$F]fluoro-2-bromoethane (FBE) by radiofluorination of 1,2-dibromoethane rather than dibromomethane. For isolation of FBE, the temperature of the preparative GC column (Porapak Q, 80/100 mesh, 7.8×700 mm) was maintained at 135° C. [$^{18}$F] fluoromethylethylcholine (FEtC) was synthesized by reaction of FBM with ethylmethylethanolamine (Pfaltz and Bauer, Waterbury Conn.) by the same procedure for synthesis of FCH. [$^{18}$F]fluoropropylcholine (FPC) was produced via the intermediate [$^{18}$F]fluorobromopropane (FBP) which was synthesized and HPLC purified as previously described (Block et al, J. Label Comp Radiopharm. 24:1029–1042 (1987)). The syntheses of FBE and FBP were not optimized, resulting in poorer radiochemical yields of FEC (<3%) and FPC (<1%), respectively, than for FCH or FEtC (30–40%).

Radiochemical purity of FCH was measured by two independent analytical HPLC systems. The first was a reverse-phase system (C-18 250×4.6 mm, 0.05M phosphoric acid and 1 mM 2-napthalenesulfonic acid in 80% water/20% methanol, 0.5 ml/min, retention time=4.4 mm) using non-radioactive fluorocholine as a reference standard. The sample was doped with 0.1 mg choline chloride before administration on the HPLC to avoid variable retention of the high specific activity [$^{18}$F]FCH on the column. The second HPLC system was based on cation-exchange as previously described for measurement of CH metabolites (Roivainen et al, Eur. J. Nucl. Med. 27:25–32 (2000)). The column was Partisil SCX (250×4.6 mm) eluted by 0.25 M sodium dihydrogen phosphate solution (pH=4.8):acetonitrile (90:10) at a flow rate of 1.8 ml/min. Radioactivity and UV-absorbance (206 nm) of the eluent were measured in-line. The retention time was 5.0, 5.4, 5.5, and 6.0 min for FCH, HARA-1, FEtC, and FPC respectively. The cation-exchange HPLC system was found to be preferable to the reverse-phase HPLC system since peak resolution was superior, and there was negligible retention of radioactivity on the column.

Stability of FCH

The stability of FCH in its prepared form was evaluated by monitoring the radiochemical purity using the HPLC system described above. Furthermore, the stability of FCH in blood was examined by incubating approximately 100 μCi FCH in a 3 ml sample of heparinized whole blood taken from healthy human subjects (n=5). After an incubation of 2 hr at 37 C, the plasma was separated, the plasma proteins precipitated by adding two volumes of methanol, and the supernatant was analyzed for intact FCH by cation-exchange HPLC.

Accumulation of Radiotracers by Human Cancer Cells

Cells (2 to 2.5×10$^5$/well) of ten different human cancer cell lines were seeded on 6-well plates and incubated for 2 days at which time >90% confluency was reached. The incubation media utilized for the experiments differed according to the cancer cell type (Table 1). On the day of the study, the medium was refreshed using a volume of 1 ml in each well. Cells were incubated in control conditions or with the addition of metabolic and growth factor receptor inhibitors to test the sensitivity of uptake of the radiotracers to specific inhibitions. The inhibitor of choline uptake and phosphorylation, hemicholinium-3 (HC-3) (Research Biochemicals, Natick, Mass.) was added to give a concentration of 5 mM. The phosphatidylinositol 3-kinase (PI-3 kinase) inhibitor, LY294002 (Calbiochem, San Diego Calif.), was utilized at a concentration of 15 M. The epidermal growth factor (EGF) receptor kinase inhibitor, AG1478 (Calbiochem), was added at a concentration of 50 nM. The concentrations of the inhibitors were 10 times their respective literature in vivo IC$_{50}$ values for choline phosphorylation (HC-3) (Hernandez-Alcoceba et al, Oncogene 15:2289 (1997)), PI-3 kinase inhibition (LY294002) (Vlahos et al, J. Biol. Chem. 269:5241 (1994)), and EGF receptor kinase inhibition (AG1478) (Osherov et al, Eur. J. Biochem. 225:1047 (1994)). Following a 30-min incubation period, the radiotracers (e.g., FDG or FCH) were added (~2 Ci/well) and the cells were incubated for 2 hr. The cells were washed three times with phosphate buffered saline solution, released from the plates by briefly incubating with 0.05% trypsin in DMEM, transferred to test tubes, and counted for F-18 radioactivity in a gamma counter. The amount of radioactivity in the cells was normalized by the dose administered to each well.

TABLE 1

Culture Media for Human Cancer Cells

| Cell Line | Medium |
| --- | --- |
| PC-3 prostate carcinoma | RPMI 1640 + 10% BCS + antibiotics (penicillin/streptomycin) |
| MDA-MB231 ER neg. breast carcinoma | RPMI 1640 + 10% BCS + L-glu + antibiotics |

TABLE 1-continued

Culture Media for Human Cancer Cells

| Cell Line | Medium |
| --- | --- |
| MCF7 ER pos. breast carcinoma | RPMI 1640 + 10% BCS + L-glu + antibiotics |
| SKOV3 ovarian carcinoma | DMEM + 10% BCS + L-glu + antibiotics |
| FaDu squamous cell carcinoma | RPMI 1640 + 10% BCS + L-glu + antibiotics |
| HCT 116 colon carcinoma | DMEM + 10% BCS + L-glu + antibiotics |
| H1080 colon carcinoma | MEM + 10% BCS + 1% NEAA + 1% pyruvate + L-glu + antibiotics |
| HEP G2 hepatocarcinoma | MEM + 10% BCS + 1% NEAA + 1% pyruvate + L-glu + antibiotics |
| #283 brain tumor | MEM "zinc option" (Gibco Labs, #86-0194) + 10% BCS + antibiotics |
| #124 brain tumor | MEM "zinc option" + 10% BCS + antibiotics |

Abbreviations: BCS-bovine calf serum; L-glu-L-glutamine (1%).

Analysis of Hydrophilic Choline/FCH Metabolites in Biological Samples

The primary hydrophilic metabolites of choline in mammals is phosphocholine and betaine. If FCH is handled biochemically similarly to CH in cancer cells, then $^{18}$F-labeled phosphorylfluorocholine (P-FCH) and fluorobetaine (FB) may be formed. In order to measure the levels of FCH, FB, and P-FCH in biological samples, a modification of the gradient-HPLC method of Pomfret et al. (Promfret et al, Anal. Biochem. 180:85–90 (1989)) was employed. $^{14}$C-labeled betaine and phosphocholine where prepared enzymatically from commercially available [methyl-$^4$C]choline (NEN Research Products, Boston, Mass.), using choline oxidase (Roivainen et al, Eur. J. Nucl. Med. 27:25–32 (2000)) and choline kinase (Ishidate et al, Methods Enzymol. 209:121–123 (1992)), respectively. The HPLC system used a microprocessor-controlled solvent delivery system and a silica column (Adsorbosphere Silica (10μ), 250×4.6 mm, Alltech, Deerfield, Ill.). The column was kept at room temperature and the flow rate was maintained at 1.5 ml/min. Buffer A contained acetonitrile/ethanol/acetic acid/1.0M ammonium acetate/water/0.1M sodium phosphate (800/68/2/3/127/10, v/v) and Buffer B contained the same constituents but in different proportions (400/68/44/881400/10, v/v). Fractions of effluent were collected every 0.5 min and first counted for $^{18}$F-radioactivity in a well-counter for experiments involving [$^{18}$F]FCH, then transferred to scintillation vials for counting for $^{14}$C-radioactivity. The column was equilibrated for 6 min with Buffer A before injection. After the injection (<100 μl), Buffer A was delivered for 6 min which eluted betaine (3 min) from the column. Over a period of 10 min, solvents were switched to 100% B using a linear gradient, during which time FCH (12.5 min) and choline (15 min) were eluted. Solvent B was then delivered for a further 9 min, eluting phosphocholine (19.5 min). Re-equilibration of the column with 100% A for 6 min preceded the next injection.

In Vitro Phosphorylation of FCH by Yeast Choline Kinase

To determine whether FCH is a substrate for choline kinase, [$^{18}$F]FCH (25–50 μCi) and [methyl-$^{14}$C]choline (CH) (2–4 μCi) were incubated in a test tube with yeast choline kinase (25 mU/ml), choline (1–10,000 μM), MgCl2 (12.5 mM), and ATP (10 mM) in Tris-HCl buffer (0.1 M, pH=8.75) for 10 min at 23 C. The test tube was gently agitated throughout the incubation period. The reaction was stopped by placing the tube in a boiling water bath for 2 min. To serve as controls, some samples were placed directly in the boiling water bath after addition of all substrates. The phosphorylated fraction of each radiotracer was isolated from the nonmetabolized fraction by anion exchange chromatography according to the method of Ishidate et al. (Methods Enzymol. 209:121–123 (1992)) and counted in a well-counter. The percentage of radioactivity converted to the phosphorylated form was calculated. Preliminary studies showed the phosphorylated fraction to rise linearly with time for incubations less than 15 min.

Analysis of FCH metabolites in PC-3 Prostate Cancer Cells

Preliminary analysis of radiolabeled metabolites of FCH and CH in PC-3 cells was performed. Cells were incubated in 6-well plates with FCH (~100 μCi)/[$^{14}$C]CH (~2 μCi) for 2 hr, followed by removal of radioactive medium and 3 rinses with phosphate buffered saline solution. Methanol (1 ml) was added to each well and the cells were lysed by maintaining the temperature at 37° C. for 30 min. The methanol phase was transferred to a glass test tube. Each well was rinsed with an additional 0.5 ml methanol which was added to the original fraction. To each tube, 3 ml chloroform and 1 ml 0.25 M sodium phosphate (pH=4.5) were added to separate lipids from water-soluble molecules. After vigorous mixing of the samples for 1 min, the two phases were separated, and a 0.5 ml aliquot of each phase was counted for $^{18}$F and $^{14}$C radioactivity. The aqueous phase was further analyzed for water-soluble metabolites using the gradient-HPLC method previously described. Radioactivity in the metabolite fractions (lipid, CH/FCH, betaine/FB, phosphocholine/P-FCH) was expressed as percentage of total radioactivity administered to each well.

Biodistribution Studies in Murine PC-3 Human Prostate Cancer Xenograft Model

Androgen independent prostate cancer cells (PC-3) suspended in matrigel (Collaborative Research, Bedford, Mass.) at a concentration of 1×106 cells/100 μl were injected subcutaneously into the flank of 4–6 week old male athymic mice (BALB/c nu/nu). The mice were maintained in pathogen-free conditions as previously described (Bullard et al, Neurosurgery 4:308–314 (1979)). Body weight and tumor volume were measured weekly and tumor volume (mm3) was calculated using the formula S2×L/2, where S and L represent the small and large diameters of the tumor, respectively.

After the tumor volume had surpassed 0.5 cm 3, the mice were anesthetized with pentobarbital (75 mg/kg) before injection of radiotracer, and remained anesthetized throughout the study. [18 F]FCH (20–40 μCi) and [$^{14}$C]choline (4 μCi) were simultaneously injected into a tail vein. A prescribed duration of time was allowed before procurement of heart, liver, lung, blood, kidney, bone (femur), brain (whole), prostate gland, tumor, bladder, and skeletal muscle. The tissues were weighed, and counted for $^{18}$F in a gamma counter, then dissolved in Solvable (Dupont, Boston Mass.) and counted for $^{14}$C in a liquid scintillation counter. For the bladder, the percentage of the injected dose in the urine was determined. For all other tissues, radiotracer uptake was calculated as:

$$\text{Uptake (\% dose kg/g)} = \frac{\text{CPM(tissue)} \times \text{Body Wt. (kg)} \times 100}{\text{Tissue Wt. (g)} \times \text{CPM (dose)}} \quad (1)$$

where CPM=counts per minute.

In a separate experiment, the biodistribution of [$^{18}$F]FDG was determined in the same animal model with a time of sacrifice of 45 min after injection.

Human Dosimetry Estimation

Tissue distribution data (% dose/g) obtained from the previously described mouse model after injection [$^{18}$F]FCH were converted to % dose/organ using the method of Kirschner et al (J. Nucl. Med. 16:248–249 (1975)). The distribution was assumed to be static after 10-min p.i. consistent with the avid trapping of the tracer in tissue. These data were entered into the MIRDOSE 3.1 program (J. Nucl. Med. 37:538–546 (1996)) to calculate dose estimates. Urinary radioactivity was assumed to be retained within the urinary bladder. Thus, assumptions were made in these calculations that would tend to overestimate the radiation dose in human imaging studies in which urinary radioactivity may be voided after the imaging study is performed. Since urinary excretion patterns in rodents are commonly more rapid than in the human, the assumption of no urinary clearance of radioactivity was precautionary. Bone uptake was distributed at the bone surfaces. The 70 kg adult male ORNL phantom was used since this would best reflect the primary study population (prostate carcinoma).

Toxicity Study

Four unanesthetized BALB/c nude mice were administered 1 mg/kg [$^{19}$F]FCH via tail vein injection and monitored for 48 hr. This dose represented an approximately 300,000 fold excess of FCH in comparison to the normal dose that a 70 kg person would receive in a [$^{18}$F]FCH study. The mice were euthanized at 48 hr.

PET Imaging Studies

The distribution of FCH in PET imaging studies was evaluated in 14 patients with prostate cancer, 14 patients with breast cancer, and 5 patients with brain tumors. Imaging was performed using the Advance PET scanner (GE Medical Systems, Milwaukee, Wis.). The intrinsic resolution of the scanner is 5 mm in all directions (DeGrado et al, J. Nucl. Med. 35:1398–1406 (1994)). In prostate cancer patients, a transmission scan of the pelvic region was obtained before administration of radiotracer. FCH (2.5–5 mCi) was administered intravenously, and dynamic imaging of the pelvis region was commenced for 20–30 min. During image reconstruction, the emission data in the pelvic region were corrected for photon attenuation using the transmission scan. Immediately following the dynamic scan, a whole-body emission scan was performed without transmission scanning for attenuation correction. The images were reconstructed using an Ordered Subset Expectation Maximum (OS-EM) algorithm. Regions-of-interest were drawn manually on the attenuation corrected images for evaluation of FCH kinetics in tissues. Standardized uptake values of FCH uptake in tissues were calculated using the attenuation-corrected images according to the equation:

$$SUV = \frac{\text{Body Wt.(g)CFCH(nCi/ml)}}{\text{Dose(nCi)}} \quad (2)$$

where CFCH is the concentration of FCH in the tumor region of interest.

In breast cancer patients, whole-body PET scans were obtained, beginning at 10 min post-administration of FCH. In patients with brain tumors, PET scans of the brain were obtained, beginning at 5 min post-administration of FCH.

Statistical Methods

Results are expressed as mean± standard deviation. Statistical analysis was performed using the student's t-test and statistical significance was inferred at $p<0.05$.

Example 1

Synthesis of [$^{18}$F]FCH

Figure 2:
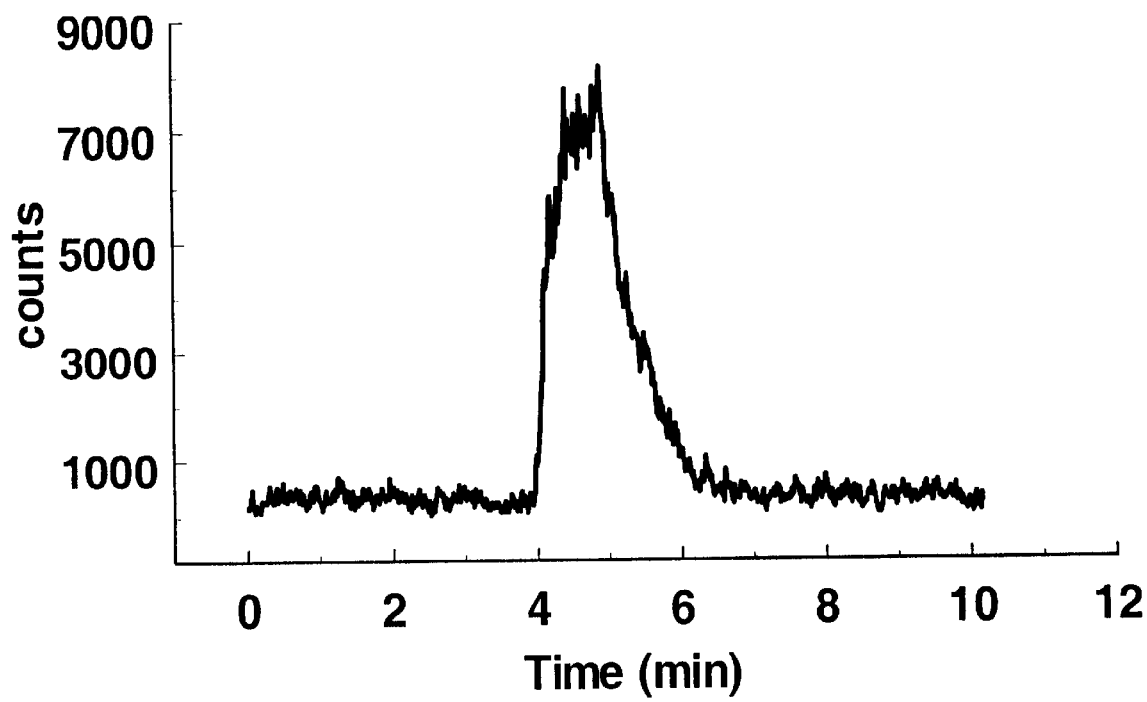
FIG. 2. Reverse phase HPLC radiochromatogram of FCH. Sample was doped with 0.1 mg choline chloride.
Figure 3A:
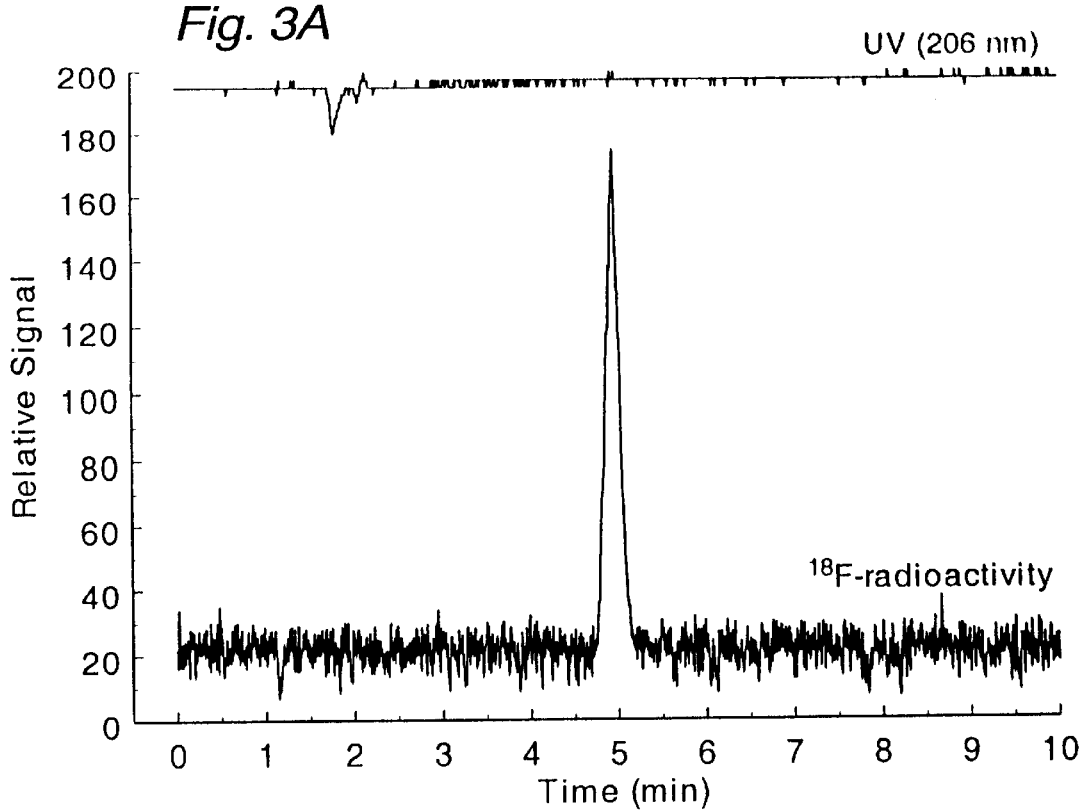
FIGS. 3A–3C. Cation-exchange HPLC radiochromatogram of (FIG. 3A) FCH, (FIG. 3B) FEC (HARA-1), and (FIG. 3C) FPC final products.
Figure 3B:
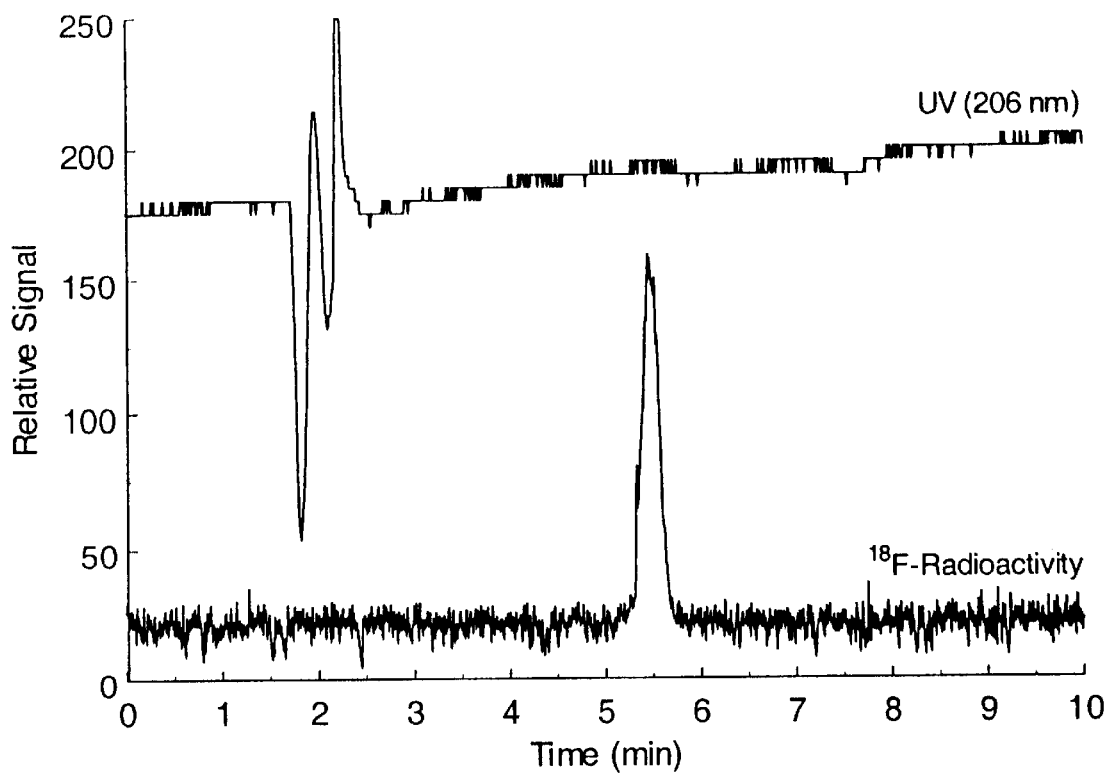
Figure 3C:
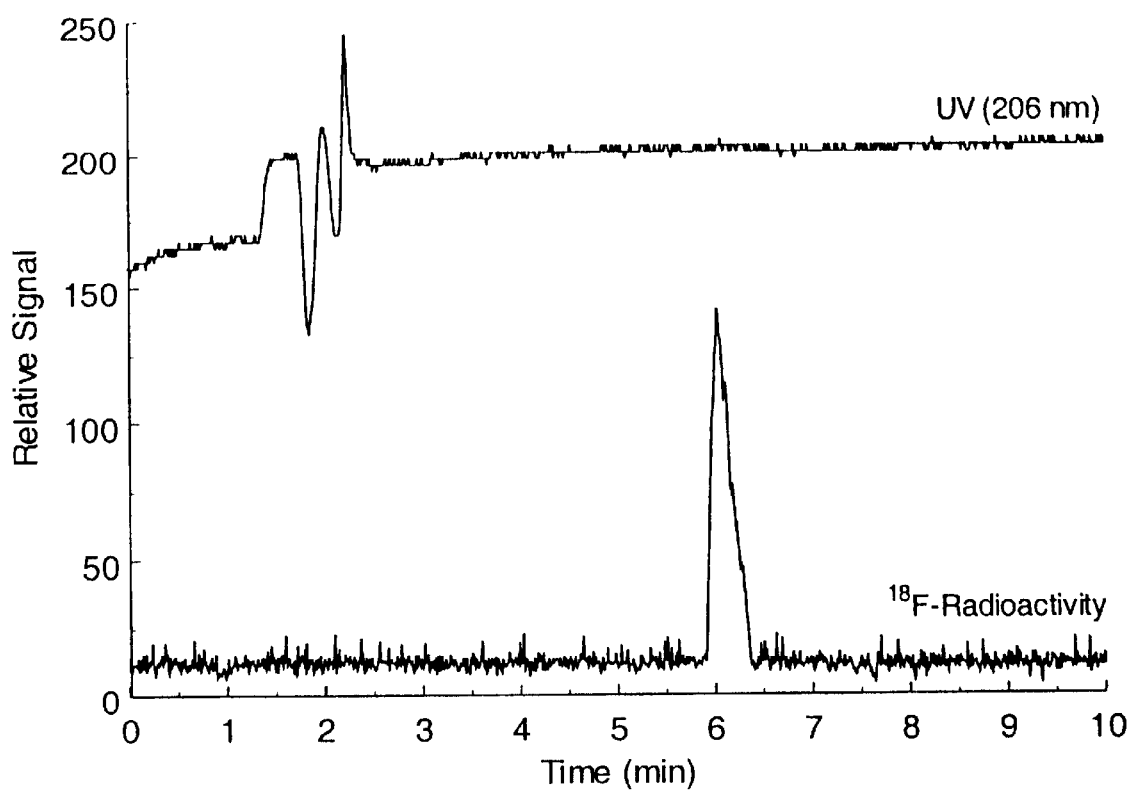

[$^{18}$F]FCH was synthesized in 20–40% radiochemical yield (not decay-corrected) in a synthesis time of less than 40 min. The radiochemical yield was determined primarily by the yield of the intermediate synthon, [$^{18}$F]FBM, since the yield of the alkylation reaction of FBM with dimethyl-ethanolamine was >90%. Radiochemical purity of >98% of FCH was verified by analytical HPLC (FIG. 2 and FIG. 3).

Example 2

Stability of FCH

The radiochemical purity of the FCH preparation was >99% as monitored by cation-exchange HPLC. The radio-chemical purity remained >99% after maintenance of the FCH preparation at room temperature for 7 hr. FCH was also found to be stable in a blood samples taken from healthy human subjects (n=5). HPLC analysis showed FCH to be completely intact after 2 hr incubations in whole blood samples at 37 C.

Example 3

In Vitro Phosphorylation of FCH by Yeast Choline Kinase

Figure 5:
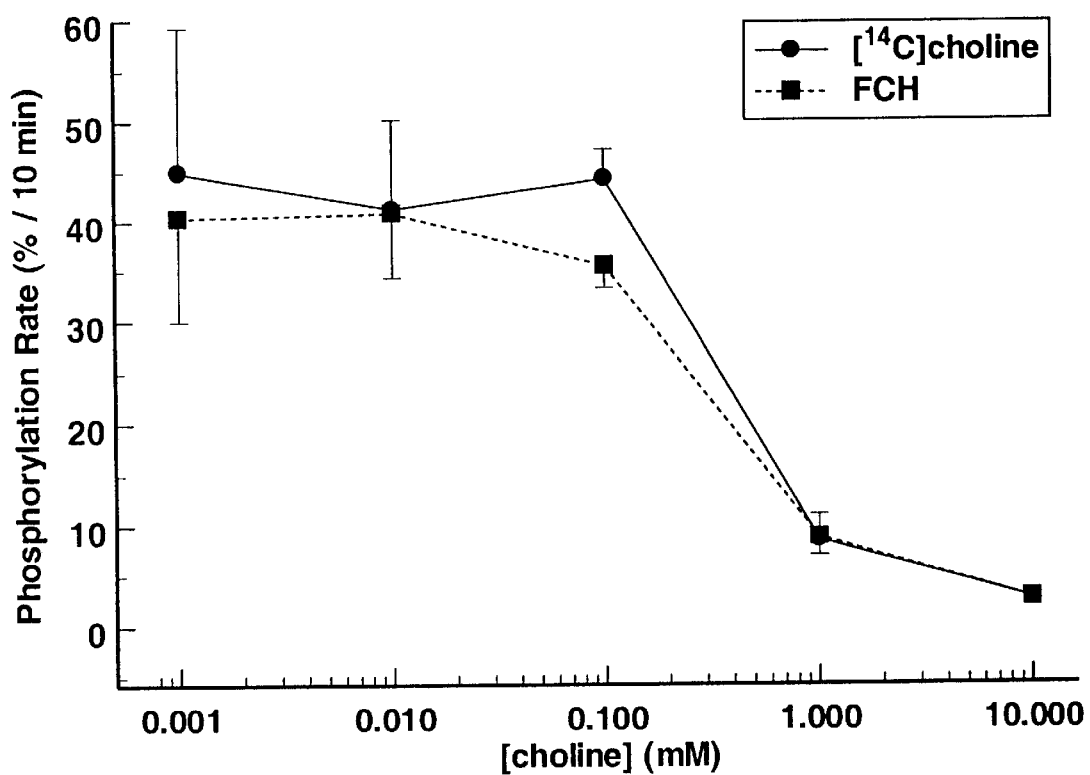
FIG. 5. In vitro phosphorylation of FCH and [$^{14}$C]choline by yeast choline kinase. Incubations were performed at room temperature with 25 mU/ml choline kinase over the range of choline concentration 0.001–10 mM. Each data point represents results mean and standard deviation of 3 samples. Similar inhibition of FCH and [$^{14}$C]choline phosphorylation at higher choline concentrations is indicative of competitive inhibition of FCH phosphorylation by choline.

To determine whether FCH is a substrate for choline kinase, [18F]FCH and [methyl-$^{14}$C]choline (CH) were incubated with yeast choline kinase (CK) (25 mU/ml) and choline (1–10,000 μM) for 10 min at 23 C. Samples quenched by boiling before incubation showed negligible phosphorylation activity. FIG. 4 shows that, after separation from unreacted FCH and [$^{14}$C]CH using an anion-exchange resin (Ishidate et al, Methods Enzymol. 209:121–123 (1992)), a single, more polar chemical product is formed from both FCH and CH. The $^{14}$C-labeled product exhibited the same retention time as an authentic standard for unlabeled phosphocholine, seen by in-line UV detection. The presence of a single $^{18}$F-labeled product, and the similar relationship of retention times between FCH and CH (FIG. 4A) and their phosphorylated products (FIG. 4B) suggests that the $^{18}$F-labeled product is phosphorylfluorocholine (P-FCH). FIG. 5 shows the dependence of phosphorylation rate on choline concentration, displaying a similar sigmoidal relationship for both radiotracers typical of Michaelis- Menten type kinetics. The apparent IC50's for inhibition of phosphorylation of radiotracer by choline were approximately 0.4 mM for both FCH and CH. The phosphorylation rates were similar for FCH and [$^{14}$C]CH at all choline concentrations. At a low choline concentration of 1 μM, phosphorylation rates of both FCH and FEtC were equivalent to CH, whereas phosphorylation rates of HARA-1 and FPC were approximately 30 and 60% less than for FCH, respectively (Table 2).

TABLE 2

In vitro phosphorylation rate and cellular uptake of radiolabeled choline analogs

| Tracer | In vitro phosphorylation¶ (%) | Uptake by PC-3 cancer cells (% dose/2 hr/105 cells plated) | |
|---|---|---|---|
| | | Control | HC-3* |
| CH | 55.9 ± 11.0 | 1.88 ± 0.25 | 1.04 ± 0.11 |
| FCH | 62.0 ± 8.8 | 1.58 ± 0.18 | 0.18 ± 0.02 |
| FEtC | 55.2 ± 6.6 | 0.74 ± 0.04** | 0.12 ± 0.02 |
| HARA-1 | 43.4 ± 3.4** | 0.32 ± 0.05** | n.a. |
| FPC | 22.1 ± 3.1** | 1.29 ± 0.28 | 0.76 ± 0.20 |

Tracers incubated in 1 μM choline, 25 mU/ml yeast choline kinase at 23° C. for 10 min (n = 5 samples each).
*5 mM hemicholinium-3.
**p < 0.01 versus FCH Example 4

Accumulation of Choline Analogs by Cultured PC-3 Prostate Cancer Cells

Under control conditions, cultured PC-3 human prostate cells accumulated FCH similarly to CH (Table 2). However, the fluoroethylated analog, HARA-1, showed only one fifth of the uptake of FCH (p<0.01). The fluoromethylethyl analog, FEtC, showed accumulation higher than HARA-1 (p<0.05), but lower than FCH (p<0.01). Uptake of the fluoropropyl analog, FPC, was not significantly different from that of FCH. Specific inhibition of choline transport and phosphorylation by hemicholinium-3 (HC-3) resulted in 89% (p<0.001), 45% (p<0.01) and 41% decreases in uptakes of FCH, CH, and FPC, respectively.

Example 5

Structure-Activity Relationships for Uptake of $^{18}$F-Labeled Choline Analogs by Human Cancer Cells The present work studies the structure-activity relationships for purposes of optimization of the molecule for imaging prostate cancer. The two primary considerations in selection of an optimal analog are: 1) maximal uptake by prostate cancer cells, and 2) minimal excretion of radioactivity into the urine for imaging of the pelvis region without presence of confounding radioactivity in the bladder. A number of structural analogs of choline were labeled as N-[$^{18}$F]fluoromethyl derivatives via the intermediate [$^{18}$F]fluorobromomethane (see Table 3). Uptake of the radiotracers was assessed in cultured PC-3 human prostate cancer cells and in a murine PC-3 xenograft model. The studies in cultured cells showed similar uptake (~2%/hr/100,000 cells plated) for [$^{18}$F]fluorocholine (FCH), the monoethyl (FEtC) and monopropyl (FPrC) analogs of FCH, [$^{18}$F]fluorohomocholine (FHC), and the α, α-dideutero-ethan-1-ol analogs of FCH, FEtC, and FPrC. All other analogs showed lower uptake, indicating poorer acceptance for high-affinity choline transport and/or choline kinase. Biodistribution studies showed prominent hepatic and renal uptake of all compounds. There were no significant differences in tumor uptake of FCH, FEtC, FPrC, and FHC (~0.07% dose kg/g). FEtC and the dideutero analog of FCH (FDC) showed low (<2% dose) excretion of radioactivity into the urine at 60 min. Urinary excretion of radioactivity was significantly higher with all other analogs (>12% dose). The low urinary radioactivity of FEtC and FDC make them favorable compounds for imaging of the pelvis region in PET studies of patients with prostate cancer.

TABLE 3

Uptake of $^{18}$F-labeled Choline Analogs by Cultured PC-3 Prostate Cancer Cells $$X-\underset{\underset{CH_2^{18}F}{|}}{\overset{\overset{Y}{|}}{N^+}}-Z$$

| | Tracer | X | Y | Z | inhibitor | Uptake by PC-3 cells % dose/2 hr/10⁵ cells plated |
|---|---|---|---|---|---|---|
| | HARA-1 | | | | none | 0.322 ± 0.054 |
| 1 | FCH | CH$_2$CH$_2$OH | CH$_3$ | CH$_3$ | none | 1.574 ± 0.033 |
| | | | | | HC-3 | 0.160 ± 0.009 |
| 2 | Ethyl (FEtC) | (CH$_2$)$_2$OH | CH$_3$ | CH$_2$CH$_3$ | none | 0.741 ± 0.041 |
| | | | | | HC-3 | 0.122 ± 0.016 |
| 3 | Propyl (FPrC) | (CH$_2$)$_2$OH | CH$_3$ | (CH$_2$)$_2$CH$_3$ | none | 1.877 ± 0.115 |
| | | | | | | HC-3 | 0.062 ± 0.001 |
| 4 | Butyl | (CH$_2$)$_2$OH | CH$_3$ | (CH$_2$)$_3$CH$_3$ | none | 0.153 ± 0.021 |
| 5 | Pentyl | (CH$_2$)$_2$OH | CH$_3$ | (CH$_2$)$_4$CH$_3$ | none | 0.073 ± 0.007 |
| 6 | Allyl | (CH$_2$)$_2$OH | CH$_3$ | CH$_2$CH=CH$_2$ | none | 4.45 ± 0.46 |
| | | | | | HC-3 | 0.11 ± 0.01 |
| 7 | Propargyl (FPP) | (CH$_2$)$_2$OH | CH$_3$ | CH$_2$C≡CH | none | 7.90 ± 0.53 |
| 8 | Isopropyl | (CH$_2$)$_2$OH | CH$_3$ | CH(CH$_3$)$_2$ | none | 0.147 ± 0.011 |
| 9 | Isobutyl | (CH$_2$)$_2$OH | CH$_3$ | CH$_2$CH(CH$_3$) | none | 2.74 ± 0.09 |
| 10 | Sec-butyl | (CH$_2$)$_2$OH | CH$_3$ | CH(CH$_3$)CH$_2$CH$_3$ | none | 0.28 ± 0.01 |
| 11 | Propanol (FHC) | (CH$_2$)$_3$OH | CH$_3$ | CH$_3$ | none | 1.635 ± 0.306 |
| 12 | Ethyl-Prop. | (CH$_2$)$_3$OH | CH$_3$ | CH$_2$CH$_3$ | none | 0.285 ± 0.023 |
| 13 | Propyl-prop. | (CH$_2$)$_3$OH | CH$_3$ | (CH$_2$)$_2$CH$_3$ | none | 0.234 ± 0.050 |

TABLE 3-continued

Uptake of $^{18}$F-labeled Choline Analogs by Cultured PC-3 Prostate Cancer Cells $$X-\overset{\overset{Y}{|}}{\underset{\underset{CH_2^{18}F}{|}}{N^+}}-Z$$

| Tracer | X | Y | Z | inhibitor | Uptake by PC-3 cells % dose/2 hr/10$^5$ cells plated |
|---|---|---|---|---|---|
| 14 Butanol | $(CH_2)_4OH$ | $CH_3$ | $CH_3$ | none | 0.140 ± 0.042 |
| 15 Diethyl | $(CH_2)_2OH$ | $CH_2CH_3$ | $CH_2CH_3$ | none | 0.503 ± 0.091 |
| 16 Diethanol | $(CH_2)_2OH$ | $CH_3$ | $(CH_2)_2OH$ | none | 0.462 ± 0.083 |
| 17 cyclic 5N | $(CH_2)_2OH$ | YZ = $(CH_2)_4$ | | none | 0.355 ± 0.028 |
| 18 cyclic 6N | $(CH_2)_2OH$ | | YZ = $(CH_2)_5$ | none | 0.144 ± 0.014 |
| 19 cyclic 6NO | $(CH_2)_2OH$ | YZ = $(CH_2)_2O(CH_2)_2$ | | none | 0.399 ± 0.014 |
| 20 cyclic N—OH | XY = $CH_2CH(OH)(CH_2)_3$ | | $CH_3$ | none | 0.077 ± 0.011 |
| 21 1-methyl | $CH_2CH(CH_3)OH$ | $CH_3$ | $CH_3$ | none | 0.202 ± 0.021 |
| 22 2-methyl | $CH(CH_3)CH_2OH$ | $CH_3$ | $CH_3$ | none | 0.182 ± 0.016 |
| 23 1,1-dideutero (FDC) | $CH_2CD_2OH$ | $CH_3$ | $CH_3$ | none | 2.410 ± 0.144 |
| 24 ethyl - D (FEDC) | $CH_2CD_2OH$ | $CH_3$ | $CH_2CH_3$ | none | 0.720 ± 0.065 |
| 25 propyl - D | $CH_2CD_2OH$ | $CH_3$ | $(CH_2)_2CH_3$ | none | 1.864 ± 0.307 |
| 26 propanol - D | $(CH_2)_2CD_2OH$ | $CH_3$ | $CH_3$ | none | 0.763 ± 0.065 |
| 27 benzyl | $CH_2CH_2OH$ | $CH_3$ | $CH_2(C_6H_5)$ | none | 0.202 ± 0.009 |
| 28 triethanol | $CH_2CH_2OH$ | $CH_2CH_2OH$ | $CH_2CH_2OH$ | none | 0.170 ± 0.045 |

Note: HC-3 - hemicholinium-3, a specific inhibitor of choline uptake and phosphorylation (5 mM); FCH - fluorocholine. FEC - fluoro-ethyl-choline; FPC - fluoro-propyl-choline; FHC - fluorohomocholine: FDC - fluoro-dideutero-choline.

Uptake of FCH was observed in all the human cancer cell types studied, including those from prostate, breast, ovarian, lung, colon, liver, and brain cancers (Table 4). These results indicate that FCH may be useful as a general probe for imaging of human cancers. Uptake of FCH was comparable to those of choline and HARA-1, although differences were observed depending on cell type. Most notably, uptake of FCH was 3-fold higher than that of HARA-1 in PC-3 prostate cancer cells. The 3 choline analogs showed significantly higher uptake than FDG in all cancer types except #283 brain tumor cells.

TABLE 4

Uptake (% dose/2 × 10$^5$ cells plated/2 hr) of Radiotracers by Cultured Human Cancer Cells

| Cell Line | [$^{14}$C]choline | [$^{18}$F]FCH | $^{18}$F-HARA-1 | [$^{18}$F]FDG |
|---|---|---|---|---|
| PC-3 prostate carcinoma | 3.170.27 | 3.290.24 | 1.130.06** | 1.490.17** |
| MDA-MB231 ER neg. breast carcinoma | 3.150.16 | 3.050.29 | 2.710.20 | 1.980.08** |
| | 3.310.67 | 3.780.55 | 3.260.47 | 1.440.41** |
| MCF7 ER pos. breast carcinoma | 3.740.93 | 3.950.04 | 3.910.10 | 0.390.02** |
| SKOV3 ovarian carcinoma | 3.340.53** | 7.310.20 | 6.280.60* | 2.920.12** |
| FaDu squamous cell carcinoma | 3.250.31** | 2.270.28 | 3.650.31** | 0.430.04** |
| HCT 116 colon carcinoma | 3.110.65** | 5.100.33 | 5.170.12 | 6.390.47* |
| H1080 colon carcinoma | 7.080.92** | 10.781.37 | 10.351.24 | 0.840.16** |
| HEP G2 hepatocarcinoma | 0.760.16* | 0.320.02 | 0.200.01** | 1.160.14** |
| #283 brain tumor | 0.390.07** | 0.150.05 | 0.080.03 | 0.230.12 |
| #124 brain tumor | | | | | p < 0.05 versus FCH in paired t-test.
**p < 0.002 versus FCH in paired t-test.

Example 6

Analysis of Metabolites of FCH and [$^{14}$C]CH in Cultured PC-3 Prostate Cancer Cells A preliminary analysis was performed regarding the chemical form of radioactivity present in PC-3 cells incubated with FCH and [$^{14}$C]CH. Cells incubated in 6-well plates for 2 hr with radiotracers were thoroughly washed to remove all extracellular radioactivity. The cells were lysed in methanol and the methanol solution added to chloroform to solubilize all lipophilic metabolites. The hydrophilic metabolites were extracted with 0.25 M sodium phosphate solution (pH=4.8) and subjected to gradient-HPLC analysis for measurement of radioactivity in the form of FCH/CH, fluorobetaine/betaine, and phosphorylfluorocholine/ phosphocholine. Table 5 shows the results expressed as percentage of administered dose to each well. Both CH and FCH were found to be undergo extensive metabolism within the PC-3 cells. Approximately 72% of $^{18}$F-radioactivity was indicated to be phosphorylfluorocholine, while 91% of $^{14}$C-radioactivity was found as phosphocholine (Table 5, FIG. 4). Radiolabeled lipophilic metabolites of FCH comprised 25% of the total $^{18}$F-radioactivity, while lipophilic metabolites of CH represented only 7% of the total $^{14}$C-radioactivity. There was a 5-fold higher incorporation of radioactivity into lipophilic species for FCH relative to [$^{14}$C]CH. Neither [$^{14}$C]betaine nor its $^{18}$F-labeled counterpart were detected by HPLC analysis, indicating that oxidation of both FCH and [$^{14}$C]CH in the cancer cells was negligible.

TABLE 5

Analysis of radioactive intracellular metabolites of [$^{14}$C]CH and FCH in cultured PC-3 cancer cells¶

| Condition | $^{14}$C-labeled species | | | $^{18}$F-labeled species | | |
|---|---|---|---|---|---|---|
| | lipophilic metabolites | hydrophilic metabolites | | lipophilic metabolites | hydrophilic metabolites | |
| | | CH | phosphocholine | | FCH | P-FCH |
| Control | 0.44 ± 0.19 | 0.16 ± 0.06 | 5.9 ± 2.3 | 2.4 ± 0.4 | 0.29 ± 0.05 | 7.1 ± 0.9 |
| +HC-3** | 0.06 ± 0.03 | 0.14 ± 0.13 | 0.08 ± 0.08* | 0.01 ± 0.01* | 0.04 ± 0.01* | 0.12 ± 0.03* |

¶Tracers incubated for 2 hr in approximately 5 × 10 5 cells at 37° C. (n = 3 samples each). Values expressed as percentage of administered dose of radioactivity following removal of radioactive medium and 3 rinses with phosphate-buffered saline. Abbreviations: FB, fluorobetaine; P-FCH, phosphorylfluorocholine.
**Uptake and phosphorylation of CH and FCH inhibited with 5 mM hemicholinium-3.
*p < 0.01 versus control condition, same radiolabel and metabolite fraction.
p < 0.01 versus $^{14}$C, same metabolite fraction and condition.

Example 7

Biodistribution of FCH in Murine PC-3 Xenograft Model

Figure 6:
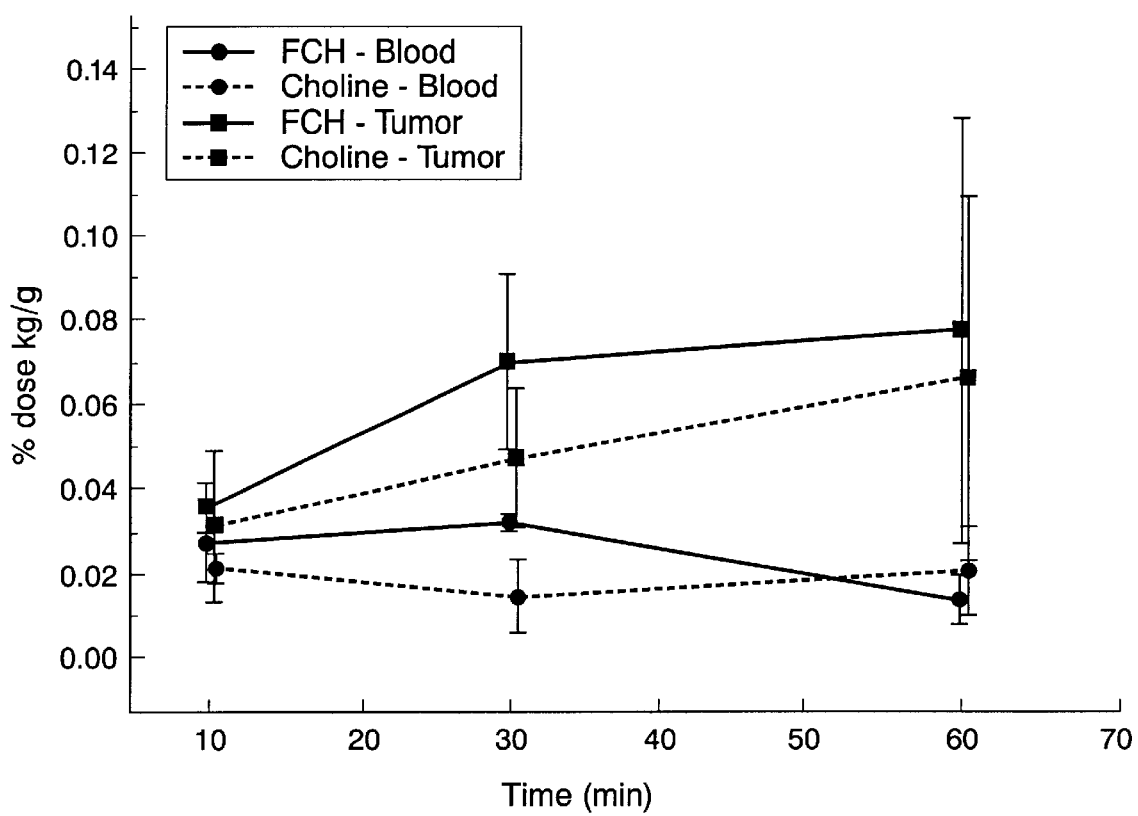
FIG. 6. Kinetics of FCH and [$^{14}$C]choline in PC-3 human prostate cancer tumor-bearing mice.

Table 6 and FIG. 6 show the biodistribution of [$^{18}$F]FCH, [$^{14}$C]CH, and [$^{18}$F]FDG in the mice. The kidneys and liver were found to be the primary sites of uptake for both FCH and CH, similar to previous findings with radiolabeled choline (Hara et al, J. Nucl. Med. 38(6):842–847 (1997), Haubrich et al, J. Pharmacol. Exp. Ther. 193:246–255 (1975)). Tumor uptake of the choline analogs and FDG were comparable at 45–60 min after injection. However, the tumor:blood ratio, a diagnostically important parameter, was higher (p<0.05) at 60 min for FCH (5.3±2.4) than for the other two tracers. Uptake of FCH by normal brain was one tenth that for FDG (p<0.0001) and one half that of CH (p<0.05). At 30 min, there was 1% and 10% of the injected dose in the urinary bladder for CH and FCH, respectively. Together with the observed slower renal clearance of radioactivity from the kidneys and lower blood radioactivity concentrations for FCH relative to CH, these findings are consistent with less reabsorption and excretion of radioactivity from the renal proximal tubular filtrate into the circulation for FCH. Liver uptake was lower (p<0.05) for FCH than for CH.

TABLE 6

Uptake (% dose kg/100 g) of radiotracers in tissues of mice with PC-3 xenografts.

| Tissue | FCH (n = 5) 10 min | FCH (n = 3) 30 min | FCH (n = 5) 60 min | CH (n = 5) 10 min | CH (n = 3) 30 min | CH (n = 5) 60 min | FDG (n = 2) 45 min |
|---|---|---|---|---|---|---|---|
| Tumor | 3.6 ± 0.6 | 7.1 ± 2.1 | 7.9 ± 5.0 | 3.2 ± 1.8 | 4.8 ± 1.6 | 6.7 ± 2.5 | 8.9 ± 0.7 |
| Blood | 2.7 ± 0.9 | 3.3 ± 0.2 | 1.5 ± 0.6 | 2.1 ± 0.3 | 1.5 ± 0.9 | 2.2 ± 1.0 | 2.8 ± 0.009 |
| Heart | 15.5 ± 5.9 | 13.2 ± 2.6 | 12.7 ± 3.2 | 20.3 ± 7.2 | 9.7 ± 1.9 | 9.1 ± 2.5 | 48.2 ± 17.9 |
| Brain | 0.8 ± 0.3 | 1.0 ± 0.2 | 0.8 ± 0.1 | 1.4 ± 0.7 | 1.0 ± 0.8 | 1.7 ± 0.6 | 8.0 ± 0.7 |
| Lung | 18.0 ± 5.3 | 17.1 ± 1.4 | 21 ± 4.4 | 26.0 ± 9.6 | 9.6 ± 6.6 | 16.7 ± 3.7 | 7.4 ± 3.1 |
| Liver | 50.7 ± 15.3 | 56.7 ± 13.2 | 58.4 ± 40.6 | 52.3 ± 11.9 | 65.2 ± 19.4 | 67.1 ± 49.7 | 1.5 ± 0.4 |
| Kidney | 127.7 ± 27.6 | 116 ± 17 | 94.3 ± 31.0 | 99.0 ± 12.9 | 53.4 ± 7.3 | 41.5 ± 15.0 | 5.3 ± 1.9 |
| Skeletal Muscle | 4.4 ± 1.8 | 1.1 ± 1.0 | 4.1 ± 0.6 | 4.7 ± 1.7 | 2.5 ± 1.5 | 2.8 ± 1.7 | 8.3 ± 0.4 |
| Prostate | 6.6 ± 2.2 | 7.1 ± 2.1 | 7.1 ± 3.0 | 9.0 ± 6.8 | 5.9 ± 2.5 | 5.5 ± 2.6 | 2.3 ± 0.4 |

The biodistribution of five structural analogs of FCH in PC-3 tumor-bearing mice are shown in Table 7. The structures of the compounds tested are given in Table 2.

The general pattern of distribution was similar for all of the analogs with high uptake noted by liver and kidney, and moderate uptake by tumor. The tumor:blood and tumor:muscle ratios were highest for the deuterated analog (FDC). These ratios are major determinants of tumor:background contrast in imaging studies.

TABLE 7

Uptake of $^{18}$F-labeled choline analogs at 60 min after injection in PC-3 prostate cancer xenograft mouse model (n = 5–6 each group)

| Tissue | Uptake (% dose kg/g) | | | | | | |
|---|---|---|---|---|---|---|---|
| | [$^{14}$C]choline | [$^{18}$F]FCH | [$^{18}$F]FDC | [$^{18}$F]FEtC | [$^{18}$F]FEDC | [$^{18}$F]FPrC | [$^{18}$F]FHC |
| Tumor | 0.067 0.043 | 0.079 0.050 | 0.066 0.004 | 0.065 0.026 | 0.079 0.027 | 0.053 0.013 | 0.043 0.005 |
| Blood | 0.022 0.010 | 0.015 0.006 | 0.0064 0.0028 | 0.015 0.004 | 0.0092 0.0039 | 0.0050 0.0025 | 0.0082 0.0021 |
| Lung | 0.167 0.037 | 0.210 0.044 | 0.270 0.146 | 0.336 0.176 | 0.360 0.147 | 0.224 0.072 | 0.165 0.043 |
| Brain | 0.017 0.006 | 0.008 0.001 | 0.011 0.004 | 0.009 0.004 | 0.009 0.003 | 0.0035 0.0010 | 0.010 0.001 |
| Liver | 0.671 0.497 | 0.584 0.406 | 0.317 0.130 | 0.525 0.226 | 0.771 0.294 | 0.828 0.435 | 0.494 0.103 |
| Kidney | 0.415 0.150 | 0.943 0.310 | 1.218 0.441 | 1.046 0.284 | 1.670 0.650 | 0.584 0.323 | 2.29 0.062 |
| Muscle | 0.028 0.017 | 0.041 0.006 | 0.025 0.017 | 0.040 0.019 | 0.051 0.023 | 0.045 0.021 | 0.023 0.005 |
| Heart | 0.091 0.025 | 0.127 0.032 | 0.170 0.049 | 0.196 0.075 | 0.208 0.074 | 0.079 0.022 | 0.190 0.038 |
| Bone | n.a. | 0.184 0.039 | 0.044 0.029 | 0.113 0.053 | 0.092 0.020 | 0.063 0.017 | 0.022 0.006 |
| Colon | n.a. | 0.123 0.052 | 0.141 0.085 | 0.177 0.077 | 0.195 0.051 | 0.204 0.103 | 0.127 0.043 |
| Bladder + urine (% dose) | 2.00 0.04 | 8.2 9.7 | 1.8 1.4 | 2.17 1.99 | 11.9 0.8 | 21.6 14.6 | 1.7 0.4 |
| Tumor:blood ratio | 3.7 2.8 | 6.4 5.7 | 12.0 5.1 | 4.4 1.9 | 9.1 1.9 | 12.7 5.6 | 5.7 2.3 |
| Tumor:muscle ratio | 1.8 1.1 | 2.0 0.5 | 3.7 1.8 | 1.7 0.7 | 1.6 0.3 | 1.3 0.7 | 1.9 0.8 |

Example 8

Human Dosimetry Estimates

Table 8 gives the radiation dose estimates to human organs as determined from calculations based on the mice FCH biodistribution data. In order to produce conservative estimates, the total body residence time was assumed to determined solely from radioactive decay (1.44×half-life= 2.6 hr). The effective dose equivalent (EDE) from a 10 mCi administration was estimated to be 1.1 rem, which is below the single-study FDA limit of 3.0 rem for research subjects. However, the largest organ dose (kidney) was 8.1 rads/rems, which is above the 5 rem single organ dose per study established by the FDA. Therefore, it was determined that the maximum administered dose in the initial studies with FCH would be 6 mCi. Refinement of these dosimetry estimates is needed using biodistribution data in humans in a subsequent study with larger numbers of subjects.

TABLE 8

Human radiation dose estimates for [$^{18}$F]FCH

| Tissue | Dose (rads/mCi) |
|---|---|
| Heart | 0.046 |
| Brain | 0.0071 |
| Lung | 0.043 |
| Liver | 0.30 |
| Kidney | 0.81 |
| Bone | 0.038 |
| Muscle | 0.032 |
| Red marrow | 0.043 |
| Testes | 0.028 |
| Ovaries | 0.039 |
| Bladder wall | 0.049 |

Example 9

Toxicity Study

Acute toxicity of 1 mg/kg body weight of [$^{19}$F]FCH was determined in four untreated BALB/c mice. No deaths were observed in the mice up to 48 hr after administration of [$^{19}$F]FCH. Neither were any behavioural/movement abnormalities observed during the monitoring period. Based on estimates of specific activity of the [$^{18}$F]FCH (2 Ci/mmol), the normal dose of FCH in the radiotracer preparation would be a factor of 300,000 times lower than the dose given in this toxicity study.

Example 10

PET Imaging in Patients with Prostate Cancer

Figure 7A:
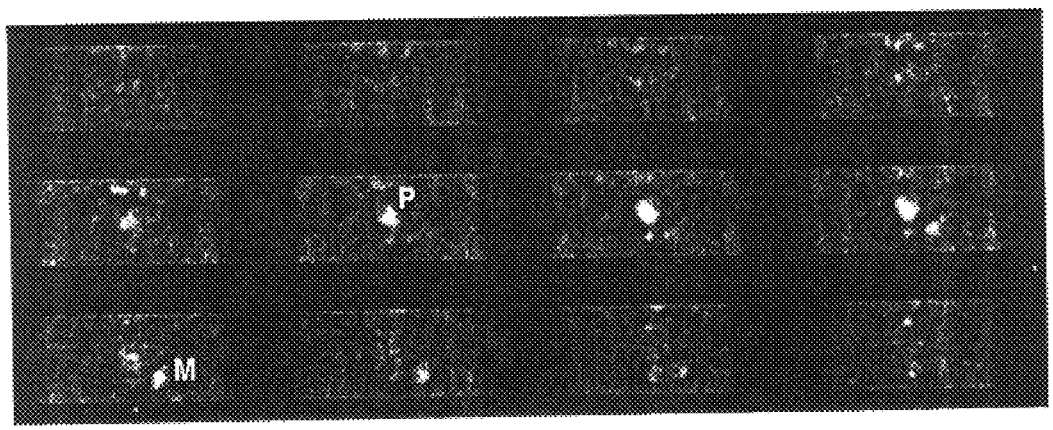
FIGS. 7A and 7B.
Figure 7B:
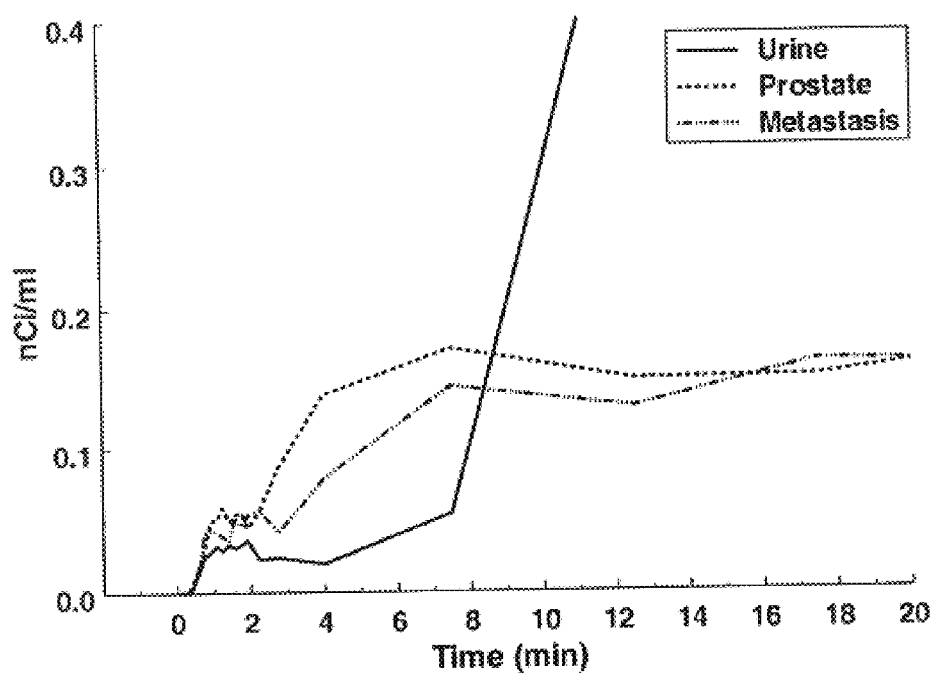

Patient 1: FCH-PET imaging of a 59 year old male with untreated locally advanced clinical stage T3 prostate cancer (PSA=22 ng/ml, Gleason grade=4,4) demonstrated accumulation of FCH in the primary prostate carcinoma and an osseous metastasis in the left ischium (FIG. 7). The latter finding was correlated with Tc-99m MDP bone scan, CT, and MRI findings of a single focus of metastatic prostate cancer. PET images acquired at 3–5 min demonstrated accumulation of FCH in the prostate gland before the arrival of activity at the bladder. FIG. 7 shows the kinetics of FCH in the prostate, metastasis, and a region-of-interest drawn within the urinary bladder. Radioactivity concentration rose rapidly in the prostate and metastasis and reached a plateau by 5 min after injection. Radioactivity began to arrive in the bladder at about 8 min after injection and the concentration increased rapidly over the next 20 min. The SUV of both the primary tumor and the metastasis was 7.7 after 5 min. Radioactivity concentration in the brain of the patient was measured to be <2% that measured in the prostate gland or metastasis. However, the pituitary gland and choroid plexus, which do not have a blood-brain barrier, showed relatively high uptake as previously noted in [$^{11}$C]CH scans (Hara et al, J. Nucl. Med. 39:990 (1998)). Also in agreement with CH distribution (Hara et al, J. Nucl. Med. 39:990 (1998)), kidneys, liver, scalp tissue and salivary glands showed notable uptake of tracer. Uptake in these normal tissues were observed in all patients and considered normal sites of FCH localization in correspondence with choline uptake by tissues. The patient was rescanned with FCH at 2 months after initiating androgen deprivation therapy at which time his PSA level had decreased to 0.9 ng/ml. Both the primary tumor and osseous metastasis were visualized in the follow-up study, however, the SUV's for FCH uptake by the tumors were substantially lower than in the initial study (SUV=3.0 in primary tumor (61% decrease), SUV=2.4 in ischial metasis (68% decrease)). Patient 2: Transmission and FCH emission scans of a 79 year old male with hormone naive clinical stage T2 prostate cancer were commenced over the lower pelvis. The prostate gland was subsequently found to be superior to the initial scans. Radioactivity uptake was demonstrated in the prostate gland in the whole-body PET image, but it was not quantifiable due to lack of attenuation correction in this region. No metastatic lesions were detected in the PET images. A recent radionuclide bone scan of the patient also showed no evidence of osseous metastases. Positioning of the prostate gland within the 15 cm field-of-view of the PET scanner in the initial attenuation-corrected scans was made difficult by the obesity of the patient (height=1.8 m, wt=147 kg).

Patient 3: FCH-PET imaging of an 80 year old male status post radical retropubic prostatectomy and bilateral scrotal orchiectomy with progressive hormone refractory prostate cancer (PSA=4,172) demonstrated extensive uptake of tracer in both bones and soft-tissue lesions (FIG. 8). SUV values in osseous lesions of the pelvis region ranged between 3.8–8.0. SUV values for soft-tissue lesions could not be quantified due to the lack of attenuation correction in the corresponding regions, but their signal intensities were similar to those of nearby osseous metastases. The same patient was scanned with FDG within the same week (FIG. 8). The FDG-PET images demonstrated fewer lesions and less pronounced uptake in the detected lesions. SUV values for FDG were approximately one half those observed for FCH in the same lesions. No radioactivity was observed in the urinary bladder on the FCH whole-body scan obtained at approximately 25–29 min after injection. Following the PET scan (at ~1 hr after injection), the patient produced 70 ml of urine that was measured to contain 1.3% of the injected dose of radioactivity. The experience in the first three patients led to modification of the scanning protocol to allow for imaging of the prostate gland with minimal chance of confounding activity in the urinary bladder: a single whole-body scan would be acquired, commencing over the pelvis 4–5 min after injection of FCH.

Figure 9A:
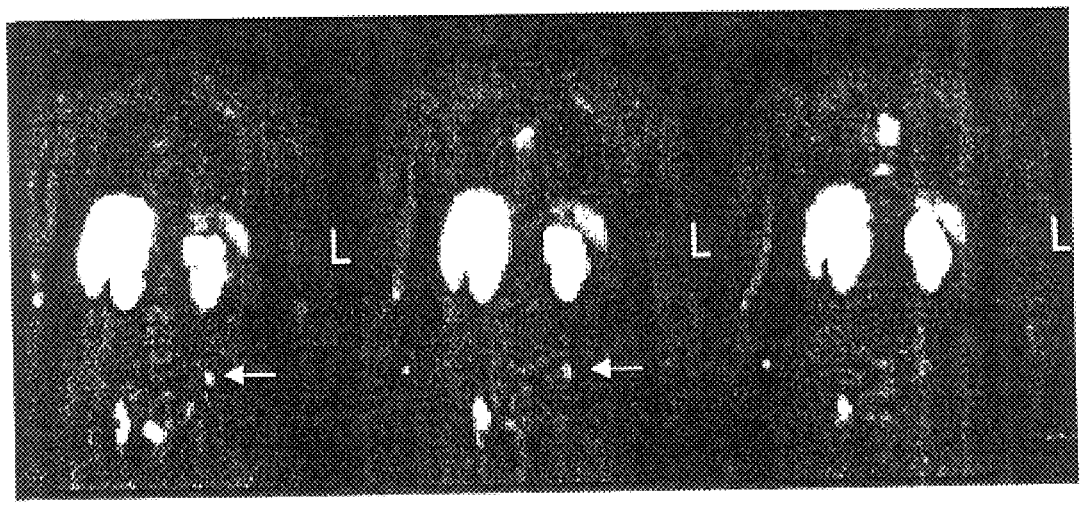
FIGS. 9A and 9B. Coronal projections of attenuation-corrected FCH-PET images in patient having clinical stage (FIG. 9A) hormone nave prostate cancer after radical prostatectomy and (FIG. 9B) in same patient two weeks after initiating androgen deprivation therapy. Slice thickness is 12.9 mm. Emission imaging was commenced over the pelvic region at 5 mm p.i., before the arrival of radioactivity at the urinary bladder. Before hormonal therapy, FCH uptake is high (SUV's exceeding 8) in several osseous and soft tissue metastases in the pelvic region and vertebrae. The accumulation of FCH in metastases is less pronounced in the follow-up study showing SUVs that were 35–40% decreased. The small focus of uptake (probably in lymph node) demonstrated by the arrow was not visualized in the follow-up study.
Figure 9B:
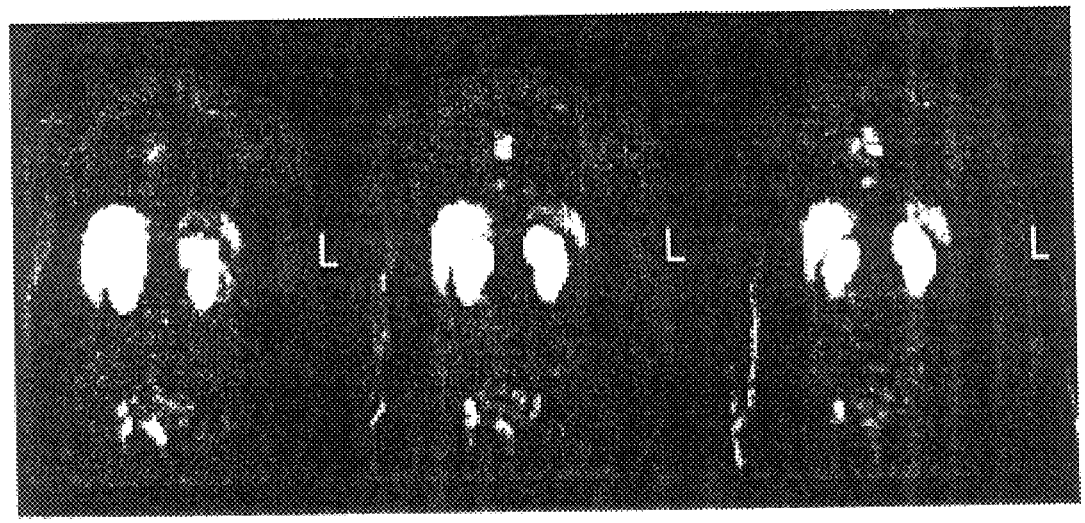

Patient 4: A 65 year old man with a history of clinical stage T3b prostate cancer treated by radical retropubic prostatectomy was diagnosed with metastatic disease by bone scan. FCH-PET imaging was performed before and after initiating androgen deprivation therapy. In the first study, whole-body emission scanning was started 5 min after injection, beginning at the pelvic region in order to image the pelvis and prostatic bed before arrival of urinary radioactivity. The images (FIG. 9) demonstrated FCH uptake (SUV's>8) in several locations consistent with both local recurrence in the prostatic bed, pelvic lymph nodes and bone. The osseous metastases seen on FCH-PET images were corroborated by recent bone scan results. The patient was rescanned 2 weeks after initiating androgen deprivation therapy. The repeat scan showed 35–40% decreases of SUV's in the various tumors (FIG. 9). Of particular note, a single lesion in the left pelvis consistent with a pelvic node lesion was not visualized on the repeat scan.

Figure 10A:
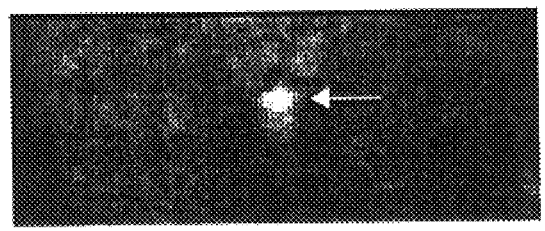
FIGS. 10A–10C.
Figure 10B:
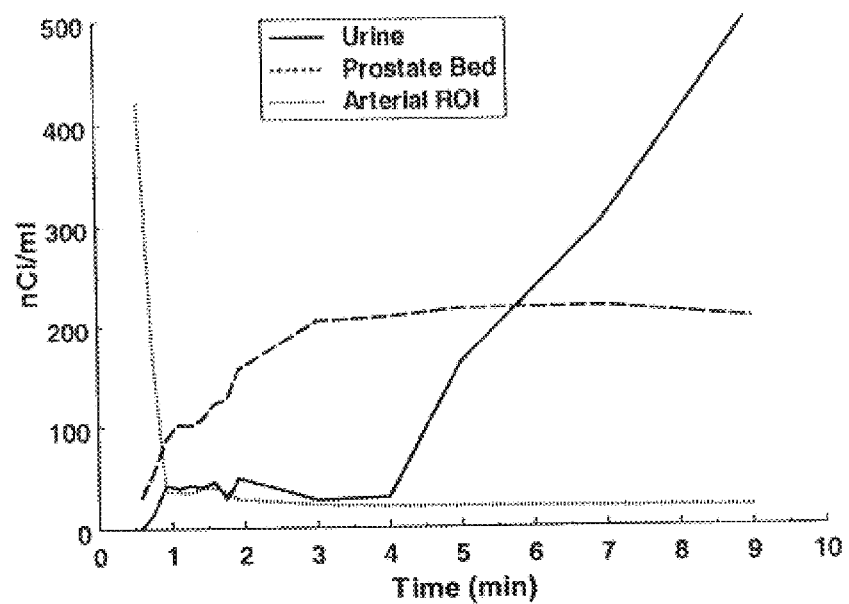
Figure 10C:
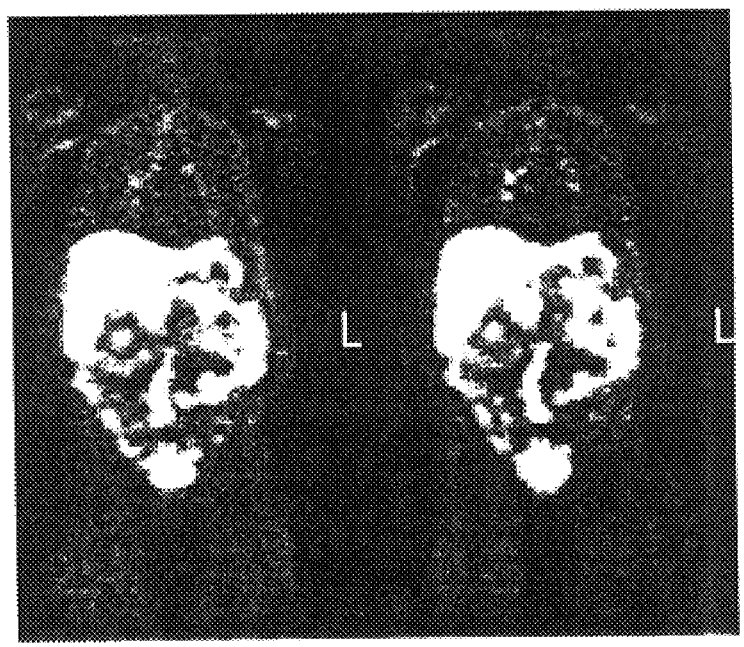

Patient 5: A 66 year old male was initially diagnosed five years prior with locally advanced clinical stage T3N0M0 prostate cancer and underwent radical prostatectomy followed by external beam radiation to the prostate bed. His post-therapy serum prostate-specific antigen (PSA) was 2.0 ng/ml. The patient was then treated with Zolex and Casodex. As his serum PSA began rising at approximately 1 yr prior to the scan, the chemotherapy was discontinued. The current serum PSA of the patient was 40.1 ng/ml. Recent radionuclide bone scans showed no abnormalities, while CT of chest, abdomen, and pelvis showed only small lymph nodes (~1 cm) in pelvis and medistinum. FCH-PET images acquired at 2–4 min demonstrated accumulation of FCH in the prostate bed before the arrival of activity at the bladder (FIG. 10A). FIG. 10B shows the kinetics of FCH in the prostate bed and regions-of-interest drawn within the urinary bladder and iliac artery. The arterial concentration of FCH peaked early and fell rapidly to <5% of the peak level within 2 min after injection, indicating extremely rapid blood clearance. Radioactivity concentration rose rapidly in the prostate bed and reached a plateau by 3 min after injection. Radioactivity began to arrive in the bladder at 4–5 min after injection and the concentration increased rapidly therafter. The whole-body images showed abnormally high foci of FCH uptake in the chest suggestive of prostate cancer within medistinal lymph nodes (FIG. 10C).

Example 11

FDC-PET Imaging in a Patient with Metastatic Prostate Cancer

A 74 year old was diagnosed 4 years prior with prostate cancer (Gleason Grade 3,4; PSA=213 ng/ml). He began androgen deprivation therapy (Lupron). At 2 years prior, a bone scan was positive in the medial right superior pubic ramus. At 1 year prior, his PSA had fallen to 16 ng/ml. He underwent a prostatectomy and orchiectomy at this time. In the last 6 months PSA rose from 24 (6 months prior) to 37 (3 months prior) to 56 (present) ng/ml. The FDC-PET scan demonstrated multiple foci of uptake suggestive of metastatic disease. Osseous lesions on the sacrum and the forementioned pubic ramus (SUV=11.7) were noted. Multiple lymphadenopathies were noted (right supraclavicular, bilateral paratracheal, subcarinal, bilateral hilar, right infrahilar, and left inguinal areas). The FDG-PET scan showed the osseous metastases seen on the FDC scan, however the extent and intensity of the lesions were relatively lower (SUV=6.5). Several foci of increased activity seen on the FDC scan were not evident on the FDG scan, including foci in the right supraclavicular region, mediastinum, and hila bilaterally. (See FIG. 11.)

Example 12

PET Imaging in Patients with Brain Tumors

PET imaging was performed in 5 patients with resected brain tumors for evaluation of recurrence of cancer. Dynamic images were obtained over the brain for the first 15 min after injection of FCH (2.5–6 mCi). Transmission scans were acquired before injection of radiotracer for purposes of attenuation correction. The results showed rapid accumulation of FCH in neoplasms at the surface of the surgical cavity; a plateau of radiotracer concentration in the tumor was reached by 5 min after injection. Radioactivity concentration in normal brain tissue was very low, allowing excellent delineation of the tumor. Comparisons of the FCH-PET images with those from conventional FDG-PET scans showed the FCH-PET to have superior tumor-background contrast. (See FIG. 12)

Example 13

PET Imaging in Patients with Breast Cancer

Thirteen patients with metastatic breast cancer and one patient with both primary and metastatic breast cancer were each imaged with both FCH-PET and FDG-PET within a period of less than one month. Low levels of FCH uptake were observed in normal subcutaneous tissue, axillary fat, normal lymph nodes, breast, lung, bone, skeletal muscle, and myocardium. High accumulation of FCH was demonstrated in normal liver, spleen and kidney. Primary and metastatic breast cancer demonstrated markedly intense FCH uptake, with a high tumor:background ratio. In all patients but one, the FCH-PET images were superior to the FDG-PET images in that the FCH images typically demonstrated more intense tumor:background uptake and greater extent of tumor involvement. In some cases, the FCH-PET revealed additional metastases that were not identified by FDG-PET.

Figure 13A:
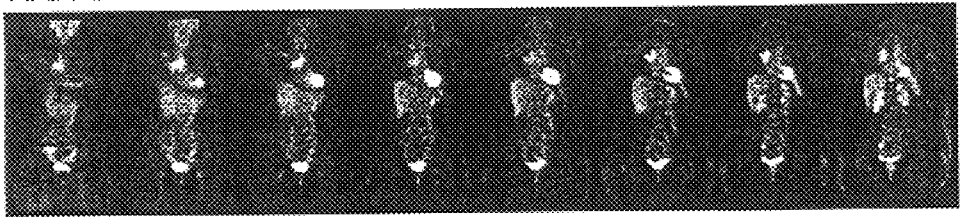
FIGS. 13A and 13B. A patient with metastatic breast cancer underwent FCH-PET and FDG-PET scanning. Myocardial uptake is only observed with FDG (FIG. 13A), whereas more prominent uptake in salivary glands, liver and kidneys is seen with FCH consistent with normal uptake of choline by these tissues (FIG. 13B). Uptake of both FDG and FCH were indicated in large metastases associated with the sternum, right hilar and paratracheal lymph nodes, and right anterior pelvis. The volume of the submanubrial metastasis was significantly larger on the FCH-PET scan. Smaller regions of focal uptake were observed on the FCH-PET scan in the right chest wall and left lung (see arrows) that were not seen on the FDG-PET scan. The uptake pattern of FDG was homogenous across the anterior pelvis metastasis, whereas FCH was taken up preferentially by the periphery of this tumor.
Figure 13B:
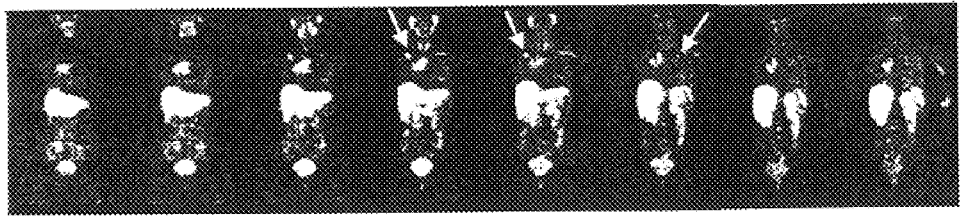

A 50 year old female had undergone re-excision of right breast intraductal carcinoma 4 yr prior, then right modified radical mastectomy 3 yr prior followed by tamoxifen chemotherapy. Six months prior to the PET scans, metastatic breast cancer was detected by palpation (right breast sternal mass) and CT (mediastinal and hilar adenopathies, mass in right anterior pelvis). Tamoxifen therapy was stopped. The FDG-PET scan showed uptake of tracer in the sternal mass (SUV=5.0), mediastinal and hilar adenopathies (SUVs~5.5) and the pelvic tumor (SUV=9.5) (FIG. 13). Uptake of FCH was also observed in the corresponding tumors: sternal mass (SUV=14.6), mediastinal and hilar adenopathies (SUVs~8.5), pelvic mass (SUV=6.5). The parasternal mass appeared significantly larger on the FCH-PET scan relative to the FDG-PET scan. Smaller metastases were indicated on the FCH-PET scan in the right chest wall and left lung that were not seen on the FDG-PET scan. Concerning the anterior pelvic tumor, there was observed a homogenous distribution of FDG across the tumor in the FDG-PET scan, whereas the FCH was preferentially distributed on the periphery of the tumor.

All documents cited above are hereby incorporated in their entirety by reference.

One skilled in the art will appreciate from a reading of this disclosure that various changes in form and detail can be made without departing from the true scope of the invention.

What is claimed is:

1. A method of monitoring radioactivity in a tissue present in the pelvis of a patient comprising:
   i) administering to said patient a radioactivity monitoring effective amount of a compound of Formula I or II

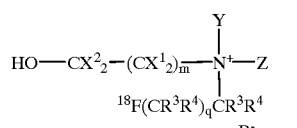

(I)

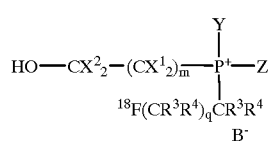

(II)

wherein

B$^-$ is a counteranion

Y=H, CH$_2$R$^1$ or CX$^3{}_2$CX$^4{}_2$—OH

Z=H, CH$_2$R$^2$, CH(CH$_3$)$_2$, CH$_2$CH=CH$_2$, CX$^5{}_2$CX$^6{}_2$OH, OCH$_3$, SCH$_3$, CH$_2$C≡CH, CH$_2$C(CH$_3$)=CH$_2$, CH$_2$(C$_6$H$_5$), CH$_2$CH(CH$_3$)$_2$, CH$_2$OCH$_3$ or CH$_2$SCH$_3$

X$^1$, X$^2$, X$^3$, X$^4$, X$^5$ and X$^6$=independently, H or deuterium

R$^1$=H, F, Cl, Br, I or CH$_3$

R$^2$=H, F, Cl, Br, I, CH$_3$ or CH$_2$CH$_3$

R$^3$=independently, H or $^{19}$F

R$^4$=independently, H or $^{19}$F m=1 or 2 q=0–2 or

Z and Y together=(CH$_2$)n, wherein n=2–6, or (CH$_2$)$_a$O (CH$_2$)$_b$, wherein a=0–4 and b=0–4, or (CH$_2$)$_a$S(CH$_2$)$_b$, wherein a=O-4 and b=0–4, and ii) detecting the presence of $^{18}$F-radioactivity in said tissue at a time prior to arrival of excreted 18F-radioactivity in the urinary bladder or ureters of said patient.

2. The method according to claim 1 wherein said compound is of Formula I.

3. The method according to claim 1 wherein said compound is of Formula II.

4. The method according to claim 1 where said tissue is neoplastic tissue.

5. The method according to claim 4 wherein said method is effected during surgery to detect or localize said neoplastic tissue.

6. The method according to claim 1 wherein said tissue is prostatic tissue, ovarian tissue, cervical tissue, lymphatic tissue, bone or bladder tissue.

7. The method according to claim 1 wherein said patient is a cancer patient that is undergoing or has undergone cancer therapy and said method is effected at more than one time point to monitor the effectiveness of said therapy.

8. The method according to claim 1 wherein said detection is effected using positron emission tomography.

9. The method according to claim 1 wherein said patient is a human.

10. A compound of Formula I

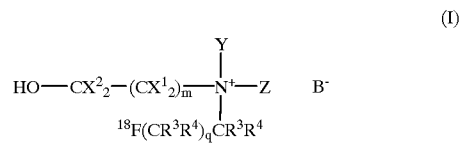

(I)

wherein

B$^-$ is a counteranion

Y=H, CH$_2$R$^1$ or CX$^3{}_2$CX$^4{}_2$—OH

Z=CH$_2$CH=CH$_2$, CX$^5{}_2$CX$^6{}_2$OH, OCH$_3$, SCH$_3$, CH$_2$C≡CH, CH$_2$C(CH$_3$)=CH$_2$, CH$_2$(C$_6$H$_5$), CH$_2$CH (CH$_3$)$_2$, CH$_2$OCH$_3$ or CH$_2$SCH$_3$

X$^1$, X$_2$, X$_3$, X$_4$, X$_5$ and X$^6$=independently, H or deuterium

R$^1$=H, F, Cl, Br, I or CH$_3$

R$^3$=independently, H or $^{19}$F

R$^4$=independently, H or $^{19}$F m=1 q=0 or

Z and Y together=(CH$_2$)n, wherein n=2–6, or (CH$_2$)$_a$O (CH$_2$)$_b$, wherein a=0–4 and b=0–4, or (CH$_2$)$_a$S(CH$_2$)$_b$, wherein a=0–4 and b=0–4.

11. A compound of Formula II

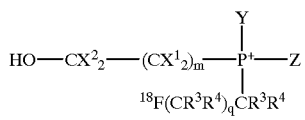

(II)

wherein

B⁻ is a counteranion

Y=H, $CH_2R^1$ or $CX^3{}_2CX^4{}_2$—OH

Z=$CH_2CH$=$CH_2$, $CX^5{}_2CX^6{}_2OH$, $OCH_3$, $SCH_3$, $CH_2C$≡$CH$, $CH_2C(CH_3)$=$CH_2$, $CH_2(C_6H_5)$, $CH_2CH(CH_3)_2$, $CH_2OCH_3$ or $CH_2SCH_3$ $X^1, X^2, X^3, X^4, X^5$ and $X^6$=independently, H or deuterium $R^1$=H, F, Cl, Br, I or $CH_3$ $R^3$=independently, H or $^{19}F$ $R^4$=independently, H or $^{19}F$ m=1 q=0 or

Z and Y together=$(CH_2)_n$, wherein n=2–6, or $(CH_2)_aO(CH_2)_b$, wherein a=0–4 and b=0–4, or $(CH_2)_aS(CH_2)_b$, wherein a=0–4 and b=0–4.

12. A composition comprising the compound of claim 10 or 11 and a pharmaceutically acceptable carrier.

13. A composition comprising a stabilizing agent and a compound of Formula I or II

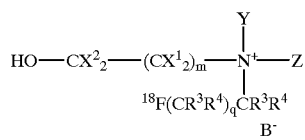

(I)

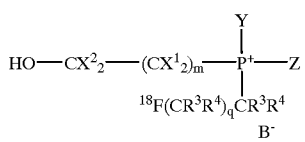

(II)

wherein

B⁻ is a counteranion

Y=H, $CH_2R^1$ or $CX^3{}_2CX^4{}_2$—OH

Z=$CH_2CH$=$CH_2$, $CX^5{}_2CX^6{}_2OH$, $OCH_3$, $SCH_3$, $CH_2C$≡$CH$, $CH_2C(CH_3)$=$CH_2$, $CH_2(C_6H_5)$, $CH_2CH(CH_3)_2$, $CH_2OCH_3$ or $CH_2SCH_3$ $X^1, X^2, X^3, X^4, X^5$ and $X^6$=independently, H or deuterium $R^1$=H, F, Cl, Br, I or $CH_3$ $R^3$=independently, H or $^{19}F$ $R^4$=independently, H or $^{19}F$ m=1 q=0 or

Z and Y together=$(CH_2)_n$, wherein n=2–6, or $(CH_2)_aO(CH_2)_b$, wherein a=0–4 and b=0–4, or $(CH_2)_aS(CH_2)_b$, wherein a=0–4 and b=0–4.

14. The composition according to claim 13 wherein said stabilizing agent is sodium L-ascorbate.

15. The composition according to claim 13 further comprising a pharmaceutically acceptable carrier.

16. A method of synthesizing a compound of Formula I or II

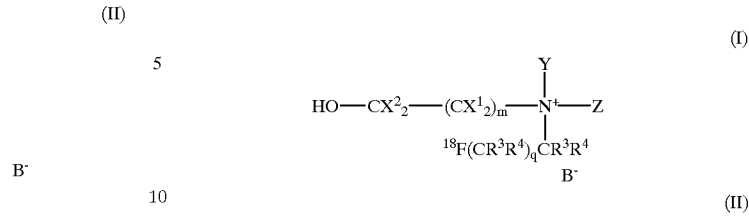

wherein

B⁻ is a counteranion

Y=$CH_2R^1$ or $CX^3{}_2CX^4{}_2$—OH

Z=$CH_2R^2$, $CH(CH_3)_2$, $CH_2CH$=$CH_2$, $CX^5{}_2CX^6{}_2OH$, $OCH_3$, $SCH_3$, $CH_2C$≡$CH$, $CH_2C(CH_3)$=$CH_2$, $CH_2(C_6H_5)$, $CH_2CH(CH_3)_2$, $CH_2OCH_3$ or $CH_2SCH_3$ $X^1, X^2, X^3, X^4, X^5$ and $X^6$=independently, H or deuterium $R^1$=H, F, Cl, Br, I or $CH_3$ $R^2$=H, F, Cl, Br, I, $CH_3$ or $CH_2CH_3$ $R^3$=independently, H or $^{19}F$ $R^4$=independently, H or $^{19}F$ m=1 or 2 q=0–2 comprising:

i) synthesizing a [$^{18}F$]fluoroalkylating agent of Formula III:

(III)

wherein $R^3$=independently, H or $^{19}F$ $R^4$=independently, H or $^{19}F$

LG=leaving group by nucleophilic radiofluorination of a precursor of Formula IV:

(IV)

wherein $R^3$=independently, H or $^{19}F$ $R^4$=independently, H or $^{19}F$

LG=leaving group using [$^{18}F$]fluoride or $H^{18}F$ and a catalyst, ii) isolating said [$^{18}F$]fluoroalkylating agent from said precursor and said catalyst using gas or liquid chromatography, iii) reacting said isolated [$^{18}F$]fluoroalkylating agent with a Formula I precursor tertiary amine or Formula II precursor tertiary phosphine alkylation substrate to form said compound of Formula I or II, and iv) isolating said compound of Formula I or II from said Formula I precursor tertiary amine or Formula II tertiary phosphine.

17. The method according to claim 16 wherein said leaving group is selected from the group consisting of a bromo-, iodo-, tosyloxy- and mesyloxy-group.

18. The method according to claim 16 wherein said catalyst is Kryptofix 2.2.2/$K_2CO_3$ or a basic tetraalkylammonium salt.

19. The method according to claim 16 wherein said isolating step (iv) is effected by transferring said compound of Formula I or II in ethanol to a cation exchange resin and washing said resin with ethanol so that said compound of Formula I or II is eluted.

20. The method according to claim 16 wherein q=0.

21. The method according to claim 20 wherein said [$^{18}$F]fluoroalkylating agent is [$^{18}$F]fluorobromomethane.

22. A method of synthesizing a compound of Formula I or II

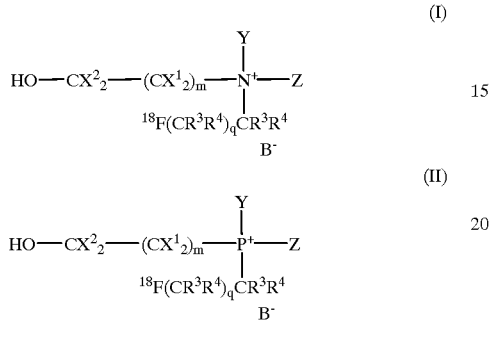

wherein
B$^-$ is a counteranion
Y=CH$_2$R$^1$ or CX$^3{}_2$CX$^4{}_2$—OH
Z=CH$_2$R$^2$, CH(CH$_3$)$_2$, CH$_2$CH=CH$_2$, CX$^5{}_2$CX$^6{}_2$OH, OCH$_3$, SCH$_3$, CH$_2$C≡CH, CH$_2$C(CH$_3$)=CH$_2$, CH$_2$(C$_6$H$_5$), CH$_2$CH(CH$_3$)$_2$, CH$_2$OCH$_3$ or CH$_2$SCH$_3$
X$^1$, X$^2$, X$^3$, X$^4$, X$^5$ and X$^6$=independently, H or deuterium
R=H, F, Cl, Br, I or CH$_3$
R$^2$=H, F, Cl, Br, I, CH$_3$ or CH$_2$CH$_3$
R$^3$=independently, H or $^{19}$F
R$^4$=independently, H or $^{19}$F
m=1 or 2
q=1 or 2
comprising:
i) preparing a hydroxyl-protected $^{18}$F-labeled choline analog of the Formula VI or VII:

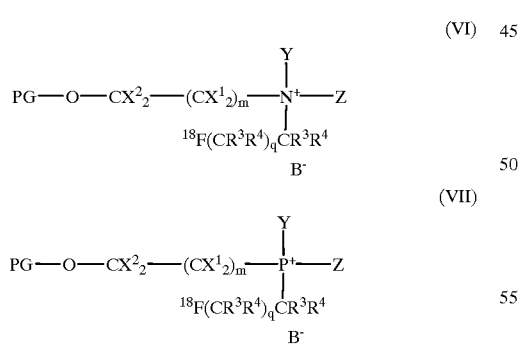

wherein
B$^-$ is a counteranion
Y=CH$_2$R$^1$ or CX$^3{}_2$CX$^4{}_2$—OH
Z=CH$_2$R$^2$, CH(CH$_3$)$_2$, CH$_2$CH=CH$_2$, CX$^5{}_2$CX$^6{}_2$OH, OCH$_3$, SCH$_3$, CH$_2$C≡CH, CH$_2$C(CH$_3$)=CH$_2$, CH$_2$(C$_6$H$_5$), CH$_2$CH(CH$_3$)$_2$, CH$_2$OCH$_3$ or CH$_2$SCH$_3$
X$^1$, X$^2$, X$^3$, X$^4$, X$^5$ and X$^6$=independently, H or deuterium R$^1$=H, F, Cl, Br, I or CH$_3$
R$^2$=H, F, Cl, Br, I, CH$_3$ or CH$_2$CH$_3$
R$^3$=independently, H or $^{19}$F
R$^4$=independently, H or $^{19}$F
m=1 or 2
q=1 or 2
PG=hydroxyl protecting group (e.g. acetyl group)
by nucleophilic radiofluorinating of a compound of Formula VIII or IX:

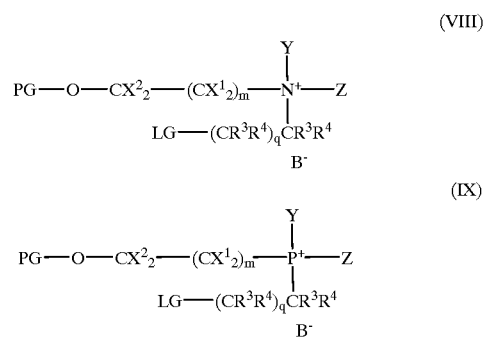

wherein
B$^-$ is a counteranion
Y=CH$_2$R$^1$ or CX$^3{}_2$CX$^4{}_2$—OH
Z=CH$_2$R$^2$, CH(CH$_3$)$_2$, CH$_2$CH=CH$_2$, CX$^5{}_2$CX$^6{}_2$OH, OCH$_3$, SCH$_3$, CH$_2$C≡CH, CH$_2$C(CH$_3$)=CH$_2$, CH$_2$(C$_6$H$_5$), CH$_2$CH(CH$_3$)$_2$, CH$_2$OCH$_3$ or CH$_2$SCH$_3$
X$^1$, X$^2$, X$^3$, X$^4$, X$^5$ and X$^6$=independently, H or deuterium
R$^1$=H, F, Cl, Br, I or CH$_3$
R$^2$=H, F, Cl, Br, I, CH$_3$ or CH$_2$CH$_3$
R$^3$=independently, H or $^{19}$F
R$^4$=independently, H or $^{19}$F
m=1 or 2
q=1 or 2
PG=hydroxyl protecting group
LG=leaving group
using [$^{18}$F]fluoride or H$^{18}$F in the presence of a catalyst,
ii) removing said PG group to form said compound of Formula I or Formula II, and
iii) isolating said compound of Formula I or II resulting from step (ii) from said precursor and catalyst.

23. The method according to claim 22 wherein said hydroxyl-protected, leaving group-substituted precursor is 3-bromopropyl-dimethyl-2-acetoxyethyl-ammonium bicarbonate.

24. The method according to claim 22 wherein said leaving group (LG) is a bromo-, iodo-, tosyloxy- or mesyloxy-group.

25. The method according to claim 22 wherein step (ii) is effected using base-catalyzed hydrolysis.

26. The method according to claim 22 wherein said isolating step (iii) is effected using high performance liquid chromatography.

27. A compound of Formula VIII or IX:

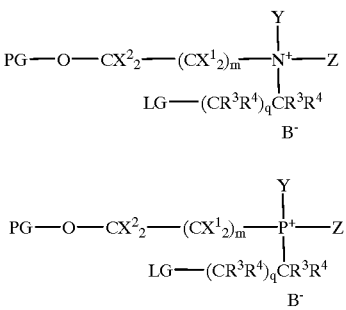

(VIII)

(IX)

wherein
 B⁻ is a counteranion
 Y=$CH_2R^1$ or $CX^3{}_2CX^4{}_2$—OH
 Z=$CH_2R^2$, $CH(CH_3)_2$, $CH_2CH=CH_2$, $CX^5{}_2CX^6{}_2OH$, $OCH_3$, $SCH_3$, $CH_2C\equiv CH$, $CH_2C(CH_3)=CH_2$, $CH_2(C_6H_5)$, $CH_2CH(CH_3)_2$, $CH_2OCH_3$ or $CH_2SCH_3$
 $X^1$, $X^2$, $X^3$, $X^4$, $X^5$ and $X^6$=independently, H or deuterium
 $R^1$=H, F, Cl, Br, I or $CH_3$
 $R^2$=H, F, Cl, Br, I, $CH_3$ or $CH_2CH_3$
 $R^3$=independently, H or $^{19}F$
 $R^4$=independently, H or $^{19}F$
 m=1 or 2
 q=1 or 2
 PG=hydroxyl protecting group
 LG=leaving group.

28. The compound according to claim 10 wherein Z=$CH_2CH=CH_2$, $CH_2C\equiv CH$, $CH_2CH(CH_3)_2$, $CH_2C(CH_3)=CH_2$, $CH_2OCH_3$, $CH_2SCH_3$.

29. The compound according to claim 11 wherein Z=$CH_2CH=CH_2$, $CH_2C\equiv CH$, $CH_2CH(CH_3)_2$, $CH_2C(CH_3)=CH_2$, $CH_2OCH_3$, $CH_2SCH_3$.

30. The compound according to claim 13 wherein Z=$CH_2CH=CH_2$, $CH_2C\equiv CH$, $CH_2CH(CH_3)_2$, $CH_2C(CH_3)=CH_2$, $CH_2OCH_3$, $CH_2SCH_3$.

* * * * *